US009877847B2

(12) United States Patent
Bettenga

(10) Patent No.: US 9,877,847 B2
(45) Date of Patent: Jan. 30, 2018

(54) DETERMINING ANATOMICAL ORIENTATIONS

(71) Applicant: SMITH & NEPHEW, INC., Memphis, TN (US)

(72) Inventor: Mason James Bettenga, Memphis, TN (US)

(73) Assignee: Smith & Nephew, Inc., Memphis, TN (US)

( * ) Notice: Subject to any disclaimer, the term of this patent is extended or adjusted under 35 U.S.C. 154(b) by 364 days.

(21) Appl. No.: 14/378,248

(22) PCT Filed: Feb. 21, 2013

(86) PCT No.: PCT/US2013/027042
§ 371 (c)(1),
(2) Date: Aug. 12, 2014

(87) PCT Pub. No.: WO2013/130326
PCT Pub. Date: Sep. 6, 2013

(65) Prior Publication Data
US 2015/0038832 A1 Feb. 5, 2015

Related U.S. Application Data

(60) Provisional application No. 61/604,612, filed on Feb. 29, 2012.

(51) Int. Cl.
*A61F 2/46* (2006.01)
*A61B 19/00* (2006.01)
(Continued)

(52) U.S. Cl.
CPC .......... *A61F 2/4657* (2013.01); *A61B 5/062* (2013.01); *A61B 5/064* (2013.01); *A61B 5/1114* (2013.01);
(Continued)

(58) Field of Classification Search
CPC ..... A61B 5/6878; A61B 5/064; A61B 5/1114; A61B 5/1127; A61B 34/10; A61B 90/39;
(Continued)

(56) References Cited

U.S. PATENT DOCUMENTS 7,001,346 B2   2/2006   White
7,634,306 B2   12/2009  Sarin
(Continued)

FOREIGN PATENT DOCUMENTS

CN   102271610 A1   12/2011
CN   102300519 A1   12/2011
(Continued)

OTHER PUBLICATIONS

Extended European Search Report issued in European Application No. 13754865.7 dated Oct. 5, 2015, 7 pages.
(Continued)

*Primary Examiner* — Katherine Fernandez
*Assistant Examiner* — Colin T Sakamoto
(74) *Attorney, Agent, or Firm* — David Chambers

(57) ABSTRACT

Methods, systems, and apparatus for determining anatomical orientations are described. Data is received that indicates a position of a reference device configured to move with a pelvis of a subject. Data is received that indicates locations corresponding to a reference surface. Data is received that indicates locations on the pelvis. One or more anatomical orientations are determined based on the locations corresponding to the reference surface and the locations on the pelvis. The anatomical orientations are registered to the reference device.

20 Claims, 13 Drawing Sheets

(51) Int. Cl.
*A61F 2/34* (2006.01)
*A61B 5/00* (2006.01)
*A61B 5/06* (2006.01)
*A61B 5/11* (2006.01)
*A61B 34/10* (2016.01)
*A61B 34/20* (2016.01)
*A61B 90/00* (2016.01)

(52) U.S. Cl.
CPC .......... *A61B 5/1127* (2013.01); *A61B 5/6878* (2013.01); *A61B 34/10* (2016.02); *A61B 34/20* (2016.02); *A61B 90/39* (2016.02); *A61F 2/34* (2013.01); *A61B 2034/107* (2016.02); *A61B 2034/2051* (2016.02); *A61B 2034/2055* (2016.02); *A61B 2090/3916* (2016.02); *A61B 2090/3975* (2016.02); *A61F 2002/469* (2013.01); *A61F 2002/4668* (2013.01); *F04C 2270/041* (2013.01)

(58) Field of Classification Search
CPC ....... A61B 34/20; A61B 5/062; A61F 2/4657; A61F 2/34
See application file for complete search history.

(56) References Cited

U.S. PATENT DOCUMENTS

| | | | |
|---|---|---|---|
| 7,660,623 | B2 | 2/2010 | Hunter |
| 7,835,784 | B2 | 11/2010 | Mire |
| 2002/0077540 | A1 | 6/2002 | Kienzle |
| 2004/0087852 | A1 | 5/2004 | Chen et al. |
| 2004/0097952 | A1 | 5/2004 | Sarin et al. |
| 2004/0147926 | A1 | 7/2004 | Iversen |
| 2004/0230199 | A1 | 11/2004 | Jansen et al. |
| 2005/0065617 | A1 | 3/2005 | Moctezuma et al. |
| 2006/0095047 | A1 | 5/2006 | de la Barrera |
| 2006/0190011 | A1 | 8/2006 | Ries |
| 2008/0021309 | A1 | 1/2008 | Amiot |
| 2008/0132783 | A1 | 6/2008 | Revie et al. |
| 2009/0164024 | A1 | 6/2009 | Rudan |
| 2009/0306679 | A1 | 12/2009 | Murphy |
| 2010/0030231 | A1 | 2/2010 | Revie |
| 2010/0249796 | A1 | 9/2010 | Nycz |
| 2012/0022406 | A1 | 1/2012 | Hladio et al. |
| 2012/0136402 | A1 | 5/2012 | Burroughs |

FOREIGN PATENT DOCUMENTS

| | | |
|---|---|---|
| WO | WO2006060632 A1 | 6/2006 |
| WO | WO2011124661 A1 | 10/2011 |
| WO | WO2012100825 A1 | 8/2012 |
| WO | WO2013049534 A1 | 4/2013 |

OTHER PUBLICATIONS

International Preliminary Report on Patentability for International Application No. PCT/US2013/027042, dated Sep. 2, 2014.
First Office Action for Chinese Application No. 201380022552.6 dated Apr. 25, 2016.
Authorized officer Han, In Ho, International Search Report/Written Opinion in PCT/US2013/027042 dated Jun. 12, 2013, 12 pages.
M. Tannast et al, "Estimation of pelvic tilt on anterioposteior X-rays—a comparison of six parameters," Skeletal Radiology, vol. 35, issue 3, pp. 149-155, 2006, 7 pages.

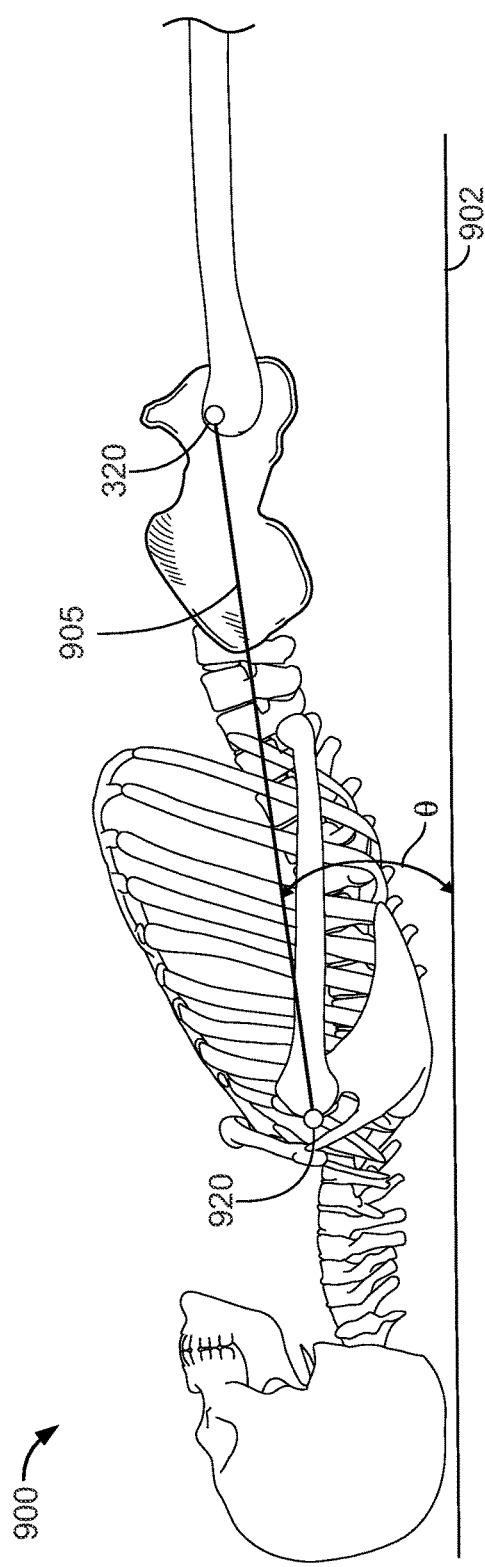
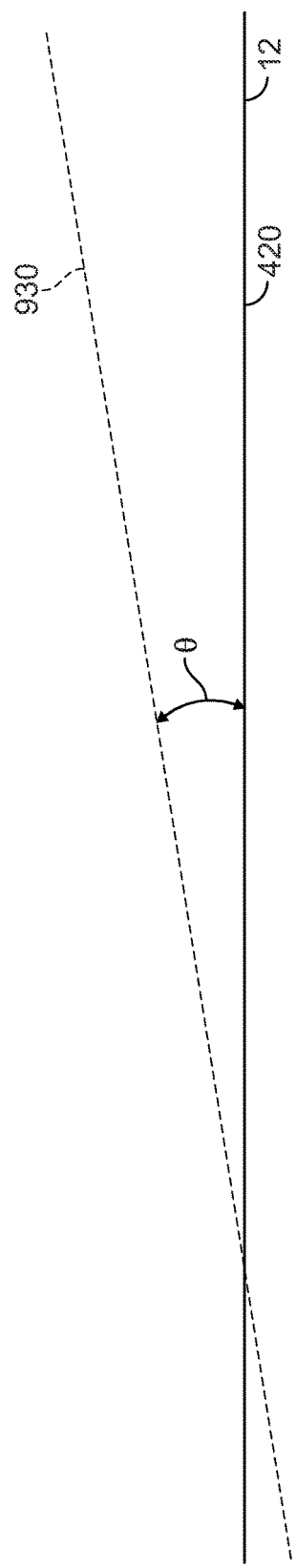
FIG. 9A
FIG. 9B

DETERMINING ANATOMICAL ORIENTATIONS

CROSS-REFERENCE TO RELATED APPLICATION

This application claims priority to and the full benefit of U.S. Provisional Application Ser. No. 61/604,612, filed Feb. 29, 2012, and titled "DETERMINING ANATOMICAL ORIENTATIONS," the entire contents of which are incorporated herein by reference.

FIELD

This disclosure relates to determining anatomical orientations.

BACKGROUND

In hip arthroplasty, an acetabulum is sometimes reamed or otherwise prepared to receive an acetabular cup implant. Proper alignment of the reamer and impactor during a hip arthroplasty procedure are important to achieve desired performance of a hip prosthesis. In some instances, improper alignment can lead to uneven wear, dislocation, or other adverse effects.

SUMMARY

In one general aspect, a method includes determining anatomical orientations based on an orientation of a reference surface and features of a pelvis. The anatomical orientations are registered to a reference device configured to move with the pelvis.

In another general aspect, an apparatus includes one or more processing devices and one or more data storage devices. The one or more data storage devices store instructions that are operable, when executed by the one or more processing devices, to cause the one or more processing devices to perform various operations. The operations include receiving data indicating a position of a reference device configured to move with a pelvis of a subject. The operations include receiving data indicating locations on a reference surface, receiving data indicating locations on the pelvis, and determining anatomical orientations based on the locations on the reference surface and the locations on the pelvis. The operations include registering the anatomical orientations to the reference device.

Implementations can include one or more of the following features. For example, the operations include determining a surgical trajectory relative to the anatomical orientations and determining a position of a tool relative to the surgical trajectory based on a position of the reference device. Determining the surgical trajectory relative to the anatomical orientations includes determining a position of an acetabular impaction axis based on the data indicating the position of the reference device. Determining the position of the acetabular impaction axis includes determining an orientation at a predetermined inclination angle and a predetermined anteversion angle relative to the anatomical orientations. The operations include outputting data indicating the orientation of the tool relative to the surgical trajectory. Receiving data indicating locations on the reference surface includes receiving data indicating at least three locations on a substantially planar surface. Determining anatomical orientations includes determining an orientation of a coronal plane of the subject based on the at least three locations.

Implementations can also include one or more of the following features. For example, the operations include receiving information indicating a pelvic tilt angle, and determining the orientation of the coronal plane of the subject includes determining the orientation of the coronal plane using information indicating the pelvic tilt angle. Receiving data indicating locations on the pelvis includes receiving data indicating at least two locations on the pelvis that are located substantially along a medial-lateral axis. Determining anatomical orientations includes determining an orientation that extends along a substantially medial-lateral direction of the subject based on the at least two locations on the pelvis. The at least two locations include locations corresponding to the left anterior superior spine of the ilium and the right anterior superior spine of the ilium.

Implementations can also include one or more of the following features. For example, the data indicating the position of the reference device configured to move with the pelvis of the subject indicates a position of the reference device corresponding to a first position of the subject lying on the reference surface. The data indicating the position of the reference device configured to move with the pelvis of the subject indicates a position of the reference device corresponding to a second position of the subject that is different from the first position. The operations include adjusting the anatomical orientations based on the position of the reference device corresponding to the second position, determining a position of a surgical axis relative to the adjusted anatomical orientations, and determining a position of a tool relative to the surgical axis based on the position of the reference device corresponding to the second position of the subject.

Implementations can also include one or more of the following features. For example, receiving the data indicating the position of the reference device includes receiving data from an electromagnetic field sensor of the reference device. Receiving the data indicating the position of the reference device includes receiving data indicating a position of a fiducial of the reference device.

Implementations can also include one or more of the following features. For example, receiving the data indicating locations on a reference surface include receiving data indicating locations of at least three different points on a planar reference surface while the subject is lying in a supine position on the planar reference surface. Receiving the data indicating locations on the pelvis may include receiving data indicating locations corresponding to a left anterior superior spine of an ilium of the pelvis and a right anterior superior spine of the ilium. Determining the anatomical orientations based on the locations on the reference surface and the locations on the pelvis may include determining an orientation of a coronal plane for the subject based on the at least three different points on the planar reference surface and determining an orientation of a transverse axis or transverse plane of the subject based on the locations corresponding to the left anterior superior spine of the ilium and the right anterior superior spine of the ilium.

Implementations can also include one or more of the following features. For example, the operations further include determining a surgical trajectory for the subject using the anatomical orientations. The operations further include, after the subject has been moved from the supine position to a lateral position, receiving data indicating the position of a surgical tool relative to the position of the reference device while the subject is in the lateral position. The operations further include determining an orientation of the surgical tool relative to the surgical trajectory based on the data indicating the position of the surgical tool relative to the position of the reference device while the subject is in the lateral position and outputting data indicating the orientation of the surgical tool relative to the surgical trajectory.

In another general aspect, a system includes a first magnetic sensor, one or more second magnetic sensors, an electromagnetic field generator, and a control unit in communication with the first magnetic sensor and the one or more second magnetic sensors. The control unit is configured to receive data indicating an orientation of the first magnetic sensor while the first magnetic sensor is coupled to a pelvis of a subject, receive data indicating different locations of the one or more second magnetic sensors when the one or more second magnetic sensors are coupled to a substantially planar reference surface, and receive data indicating different locations of the one or more second magnetic sensors when the one or more second magnetic sensors are coupled to different locations on the pelvis. The control unit is configured to determine orientations of one or more anatomical reference planes of the subject based on the locations of the one or more second magnetic sensors and register the orientations of the one or more anatomical reference planes to the first magnetic sensor.

In another general aspect, a system includes a first reference device, one or more second reference devices, a communication module in communication with the first reference device and the one or more second reference devices, and a control unit operably coupled to the communication module. The control unit is configured to receive data indicating an orientation of the first reference device while the first reference is coupled to a pelvis of a subject, receive data indicating different locations of the one or more second reference devices when the one or more second reference devices are coupled to a substantially planar reference surface, and receive data indicating different locations of the one or more second reference devices when the one or more second reference devices are coupled to different locations on the pelvis. The control unit is configured to determine orientations of one or more anatomical reference planes of the subject based on the locations of the one or more second reference devices and register the orientations of the one or more anatomical reference planes to the first reference device.

In another general aspect, a method includes determining a first orientation relative to a subject based on an orientation of a reference surface, determining a second orientation that extends along a substantially medial-lateral direction of the subject based on features of a pelvis of the subject, and registering the first orientation and the second orientation to a reference device that is configured to move with the pelvis.

Implementations can include one or more of the following features. For example, the method includes determining a third orientation that extends perpendicular to the first orientation and the second orientation and registering the third orientation to the position of the reference device. Determining the first orientation includes determining an orientation of a coronal plane for the subject, determining the second orientation includes determining an orientation of a transverse axis; and determining the third orientation includes determining an orientation of a sagittal plane for the subject. The method includes determining a surgical trajectory using the first orientation, the second orientation, and the orientation of the reference device. Determining the surgical trajectory includes determining the trajectory at a predetermined inclination angle and a predetermined anteversion angle. The method includes determining an orientation of a tool relative to the surgical trajectory using the reference device. Determining the first orientation includes determining the first orientation based on the orientation of the reference surface and a pelvic tilt angle. Determining the first orientation includes determining the first orientation based on data indicating three or more locations on the reference surface.

Implementations can also include one or more of the following features. For example, determining the second orientation includes determining the second location based on data that indicates a location corresponding to the left anterior superior spine of the ilium and data that indicates a location corresponding to the right anterior superior spine of the ilium. Determining the second orientation that extends along the substantially medial-lateral direction of the subject based on features of the pelvis of the subject includes determining the second orientation based on data indicating positions of a probe while the probe is engaged with skin of the subject that covers the pelvis, the probe including a fiducial or a magnetic sensor. Registering the first orientation and the second orientation to the reference device that is configured to move with the pelvis includes registering the first orientation and the second orientation to a position of the reference device while the subject is positioned in a first position that is supine relative to the reference surface.

Implementations can also include one or more of the following features. For example, the method includes determining an updated position of the reference device, the updated position corresponding to a second position of the subject that is not a supine position relative to the reference surface, and determining orientations relative to the subject that correspond to the orientations of the first orientation and second orientation relative to the subject based on the updated position of the reference device. Registering the first orientation and the second orientation to the reference device that is configured to move with the pelvis includes determining the position of the reference device based on data generated by a magnetic sensor of the reference device. Registering the first orientation and the second orientation to the reference device that is configured to move with the pelvis includes determining the position of the reference device based on data indicating the position of a fiducial of the reference device.

In another general aspect, a method of determining anatomical orientations includes positioning a subject against a reference surface and attaching a reference device to a pelvis of the subject such that the reference device is configured to move with the pelvis. The method includes engaging a probe against the reference surface to measure an orientation of the reference surface, engaging a probe against the subject to measure two locations corresponding to features of the pelvis, positioning a surgical tool relative to the pelvis based on a position of the reference device.

Implementations can include one or more of the following features. For example, positioning the surgical tool relative to the pelvis based on the position of the reference device includes aligning the surgical tool relative to a surgical trajectory, the orientation of the surgical trajectory relative to the subject being defined based on the orientation of the reference surface and the two locations corresponding to features of the pelvis. The method includes moving the subject from the supine position to a lateral position, and aligning the surgical tool relative to the surgical trajectory includes aligning the surgical tool relative to the surgical trajectory while the subject is in the lateral position. Engaging a probe against the subject to measure two locations corresponding to features of the pelvis includes engaging the probe to extracutaneous locations corresponding to a left anterior superior spine of the ilium and a right anterior superior spine of the ilium of the pelvis.

In another general aspect, an apparatus includes one or more processing devices, and one or more data storage devices storing instructions that are operable, when executed by the one or more processing devices, to cause the one or more processing devices to perform various operations. The operations include receiving data indicating a position of a reference device configured to move with a pelvis of a subject, receiving data indicating locations on a reference surface, and receiving data indicating locations on the pelvis. The operations also include determining a first anatomical orientation of the subject based on the data indicating the locations on the reference surface, determining a second anatomical orientation that extends along a substantially medial-lateral direction based on the data indicating the locations on the pelvis, and registering the first anatomical orientation and the second anatomical orientation to the reference device.

Implementations may include one or more of the following features. For example, the operations may include determining a surgical trajectory based on the first anatomical orientation and the second anatomical orientation, determining a position of a tool relative to the surgical trajectory based on a position of the reference device, and outputting data indicating the position of the tool relative to the surgical trajectory. Determining the surgical trajectory based on the first anatomical orientation and the second anatomical orientation comprises determining an orientation at a predetermined inclination angle and a predetermined anteversion angle relative to the first anatomical orientation and the second anatomical orientation. The operations include determining a third anatomical orientation of the subject that is orthogonal to the first anatomical orientation and the second anatomical orientation, and registering the third anatomical orientation to the reference device that is configured to move with the pelvis. Receiving data indicating locations on the reference surface comprises receiving data indicating at least three locations on a substantially planar surface. Determining the first anatomical orientation comprises determining an orientation of a coronal plane of the subject based on the at least three locations. The operations further comprise receiving information indicating a pelvic tilt angle. Determining the orientation of the coronal plane of the subject comprises determining the orientation of the coronal plane using information indicating the pelvic tilt angle. Receiving data indicating locations on the pelvis comprises receiving data indicating at least two locations on the pelvis that are located substantially along a medial-lateral axis. Determining the second anatomical orientation comprises determining an orientation of a transverse plane of the subject based on the data indicating at least two locations on the pelvis, the orientation of the transverse plane being orthogonal to the orientation of the coronal plane of the subject. The at least two locations include locations corresponding to a left anterior superior spine of an ilium of the pelvis and a right anterior superior spine of the ilium. The data indicating the position of the reference device configured to move with the pelvis of the subject indicates a position of the reference device corresponding to a first position of the subject lying on the reference surface. The data indicating the position of the reference device configured to move with the pelvis of the subject indicates a position of the reference device corresponding to a second position of the subject that is different from the first position. The operations include adjusting the anatomical orientations based on the position of the reference device corresponding to the second position, determining a position of a surgical axis relative to the adjusted anatomical orientations, and determining a position of a tool relative to the surgical axis based on the position of the reference device corresponding to the second position of the subject. Receiving the data indicating the position of the reference device comprises receiving data indicating a position of an electromagnetic field sensor or a fiducial of the reference device.

Implementations may include one or more of the following features. For example, receiving the data indicating locations on a reference surface comprises receiving data indicating locations of at least three different points on a planar reference surface while the subject is lying in a supine position on the planar reference surface. Receiving the data indicating locations on the pelvis comprises receiving data indicating locations corresponding to a left anterior superior spine of an ilium of the pelvis and a right anterior superior spine of the ilium. Determining the first anatomical orientation includes receiving data indicating a pelvic tilt angle and determining an orientation of a coronal plane of the subject based on the at least three different points on the planar reference surface and the data indicating the pelvic tilt angle. Determining the second anatomical orientation comprises determining an orientation of a medial-lateral axis or transverse plane of the subject based on the locations corresponding to the left anterior superior spine of the ilium and the right anterior superior spine of the ilium. The operations further comprise determining a surgical trajectory for the subject using the first anatomical orientation and the second anatomical orientation, and after the subject has been moved from the supine position to a lateral position, receiving data indicating the position of a surgical tool relative to the position of the reference device while the subject is in the lateral position. The operations include determining an orientation of the surgical tool relative to the surgical trajectory based on the data indicating the position of the surgical tool relative to the position of the reference device while the subject is in the lateral position, and outputting data indicating the orientation of the surgical tool relative to the surgical trajectory.

In another general aspect, a system includes a first reference device, one or more second reference devices, a communication module in communication with the first reference device and the one or more second reference devices, and a control unit operably coupled to the communication module. The control unit is configured to perform a variety of operations. The operations include receiving data indicating an orientation of the first reference device while the first reference device is coupled to a pelvis of a subject; receiving data indicating different locations of the one or more second reference devices when the one or more second reference devices are coupled to a substantially planar reference surface; receiving data indicating different locations of the one or more second reference devices when the one or more second reference devices are coupled to different locations on the pelvis; determining a first anatomical orientation of the subject based on the data indicating the different locations of the one or more second reference devices when the one or more second reference devices are coupled to a substantially planar reference surface; determining a second anatomical orientation that extends along a substantially medial-lateral direction of the subject based on the data indicating the different locations of the one or more second reference devices when the one or more second reference devices are coupled to the different locations on the pelvis; and registering the orientations of the one or more anatomical reference planes to the first reference device.

The details of one or more implementations are set forth in the accompanying drawings and the description below. Other features, objects, and advantages will be apparent from the description and drawings, and from the claims.

DESCRIPTION OF DRAWINGS

FIGS. 9A and 9B are diagrams representing use of a pelvic tilt angle.

Like reference symbols in the various drawings indicate like elements.

DETAILED DESCRIPTION

Figure 1:
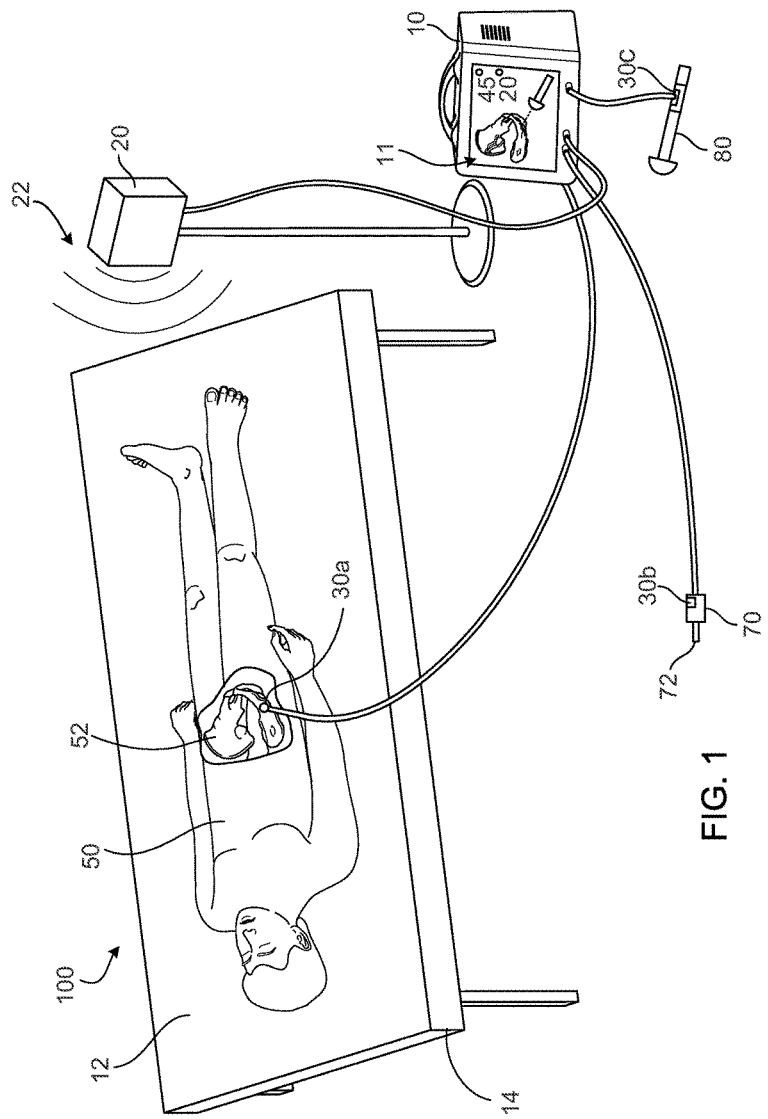
FIG. 1 is a diagram of an example of a system that can determine anatomical orientations.

Referring to FIG. 1, a spatial tracking system 100 includes a control unit 10, a position tracking device such as an electromagnetic field generator 20, and two or more reference devices such as magnetic sensors 30a-30c. The system 100 also includes a probe 70 and a surgical tool 80, such as a reamer or an impactor. The control unit 10 tracks spatial positions of the magnetic sensors 30a-30c, for example, by determining relative positions of the magnetic sensors 30a-30c and the electromagnetic field generator 20.

The system 100 can be used to determine anatomical orientations, which can include positions and directions having defined relationships relative to an anatomy. The anatomical orientations can be orientations relative to a subject 50, for example, a patient undergoing hip arthroplasty or other surgery. As described further below, the anatomical orientations are determined, at least in part, based on the orientation of a reference surface 12, for example, a surface of a surgical table 14 that the subject 50 rests against or is positioned upon, or a vertical surface, such as a wall, that the subject 50 is positioned against. The anatomical orientations of the subject 50 are registered to one of the magnetic sensors 30a that is configured to move with, for example, a pelvis 52 of the subject 50. For example, the magnetic sensor 30a can be located in a housing (not shown) that threadedly engages or is otherwise fixedly attached to pelvic bone.

Movement of the magnetic sensor 30a (and thus movement of the pelvis 52) is tracked by the system 100, permitting the system 100 to compensate for movement of the subject 50 in an operating theater. As the control unit 10 detects changes in the position of the magnetic sensor 30a, the control unit 10 adjusts the anatomical orientations to reflect corresponding changes in position. In this manner, the control unit 10 can maintain accurate anatomical orientations in the operating theater when the position of the subject 50 changes.

Using the anatomical orientations, the control unit 10 can determine and indicate surgical orientations, for example, a surgical trajectory for reaming an acetabulum of the pelvis 52 or impaction of an acetabular cup. The surgical trajectory can be an axis defined at a desired inclination angle and anteversion angle relative to the anatomical orientations of the subject 50.

In many arthroplasty procedures, pre-operative 3D imaging is used to determine surgical orientations and to adjust or create alignment tools for use during surgery. Alternatively, or in addition to 3D imaging, the system 100 can be used to intraoperatively define surgical alignments relative to the anatomy of the subject 50. Thus, the expense of MRI imaging or computed tomography (CT) imaging can often be avoided using the techniques described herein. In addition, the radiation exposure of CT imaging can be avoided.

In further detail, the electromagnetic field generator 20 produces electromagnetic fields 22 that can be detected by the magnetic sensors 30a-30c. The electromagnetic field generator 20 can have a generally plate-like shape and can also have other shapes. The electromagnetic field generator 20 can be supported by a floor-standing mount, as illustrated, or can alternatively be placed at another location. The electromagnetic field generator 20 can be handheld or can be coupled to moveable instruments.

The magnetic sensors 30a-30c can include, for example, an electromagnetic field sensor (not shown), which may include one or more inductive coils. The magnetic sensors 30a-30c can include one or more of, for example, a Hall effect sensor, a fluxgate magnetic field sensor, and a magneto-resistive sensor, in addition to or instead of one or more inductive coils. The magnetic sensor 30b can be attached to the probe 70, permitting the position of the probe 70 to be tracked by the system 100. The magnetic sensor 30c can be attached to the surgical tool 80, permitting the position of the surgical tool 80 to be tracked by the system 100.

When a magnetic sensor 30a-30c detects sufficient electromagnetic field energy from the electromagnetic fields 22, it produces signals indicating the position of the magnetic sensor 30a-30c relative to the electromagnetic field generator 20. The magnetic sensors 30a-30c transmit the signals, or data related to the signals, to the control unit 10 over a wired or wireless connection. The control unit 10 receives the signals or other position data and, determines positions of the magnetic sensors 30a-30c. The control unit 10 can control the electromagnetic field generator 20 to produce electromagnetic fields with known characteristics. In some implementations, the control unit 10 uses information about the electromagnetic fields 22 produced by the electromagnetic field generator 20, for example, information about the timing or other characteristics of the electromagnetic fields 22, to determine positions of the magnetic sensors 30a-30c relative to the electromagnetic field generator 20.

The control unit 10 includes a control module configured to, for example, supply power and control signals to regulate the operation of devices in communication with the control unit 10. The control unit 10 includes an input module to receive information from sensors and other systems. Using the information received, a processing module of the control unit 10 calculates anatomical orientations and preferred orientations of instruments 30 and tissues. The processing module also calculates the current positions of instruments and differences from the preferred orientations. The control unit 10 also includes an output module that can indicate preferred orientations and actual orientations of instruments and tissues on a user interface 11. For example, the user interface 11 can display a representation of the pelvis 52 and the surgical tool 80, and can indicate the position of the surgical tool 80 relative to the pelvis 52.

The control unit 10 can track locations and orientations using one or more coordinate reference systems. For example, the control unit 10 can define positions relative to a global reference frame that defines positions in a 3D space. In addition, or as an alternative, the control unit 10 can also define positions relative to particular locations or devices, for example, by determining positions in a coordinate reference frame defined relative to the electromagnetic field generator 20 or, for example, one of the magnetic sensors 30a-30b. One or more transformation matrices can be used to determine positions of different reference devices relative to each other, and to translate positions from one coordinate reference frame to another.

The magnetic sensors 30a-30c, the electromagnetic field generator 20, and the control unit 10 can include features as described in WIPO International Publication Nos. WO2008/106593 and WO2009/108214, each of which is incorporated herein by reference in its entirety, and as described in U.S. patent application Ser. Nos. 12/758,747 and 12/768,689, each of which is incorporated herein by reference in its entirety.

The probe 70 includes an end 72, such as a narrow tip, that has a known offset from the position of the magnetic sensor 30b. Using the offset, the control unit 10 can determine the location of the probe end 72 based on data produced by the magnetic sensor 30b. To measure a location, an operator presses a button or activates another trigger, causing the control unit 10 to measure and record the location of the probe end 72 based on the current position of the sensor 30b. In some implementations, the control unit 10 automatically measures a location in response to the probe end 72 engaging an object. The probe end 72 can include an element that is responsive to contact, such as a pressure-sensitive element or a depressible element. When contact with the probe end 72 occurs, the probe 70 sends a signal to the control unit 10, triggering the control unit 10 to record the location of the probe end 72.

Figure 2:
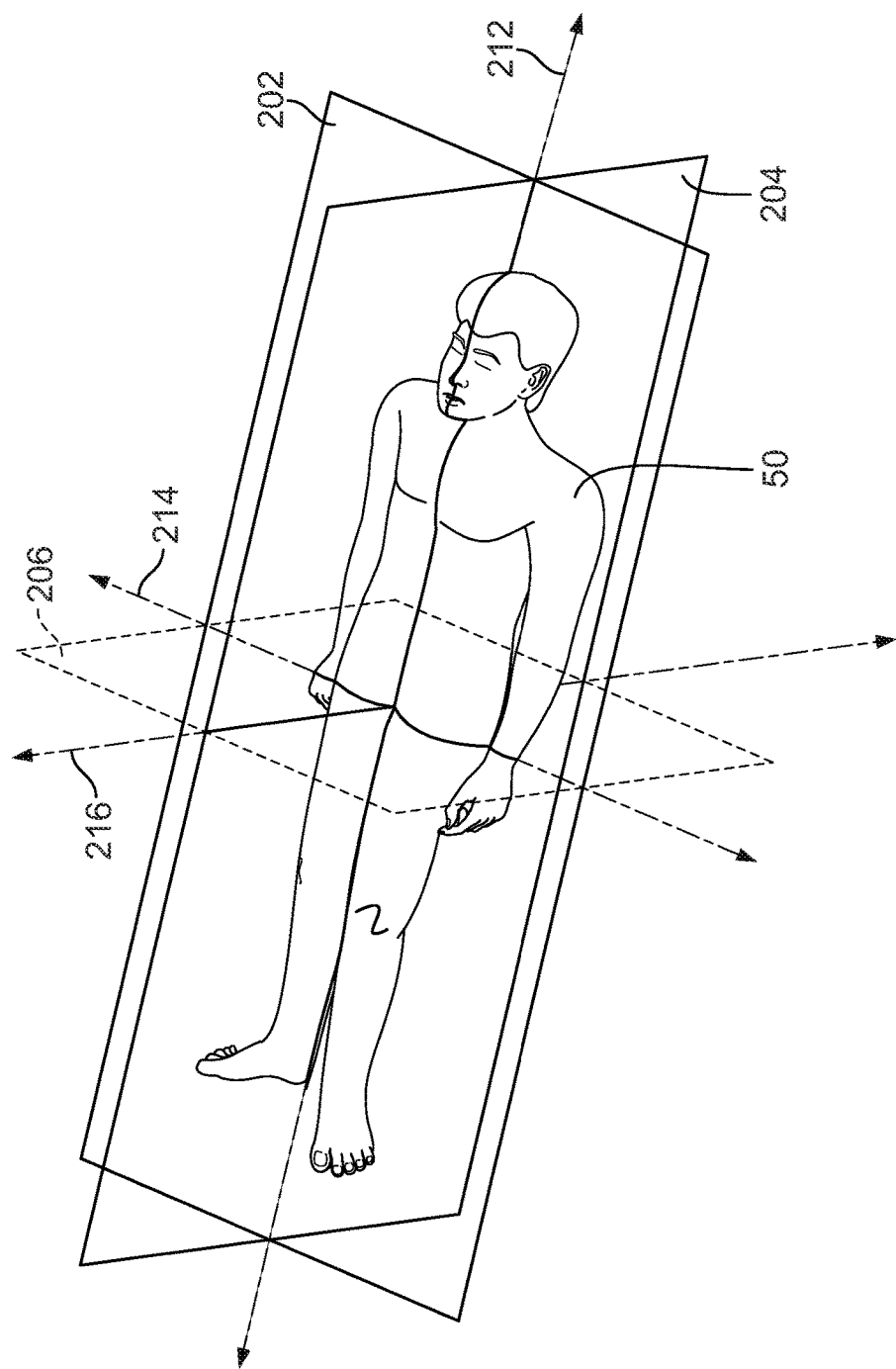
FIG. 2 is a perspective diagram illustrating examples of anatomical reference orientations.

Referring to FIG. 2, various examples of anatomical orientations are illustrated relative to the subject 50. Anatomical orientations include positions and directions having defined relationships relative to the anatomy of the subject 50. Anatomical reference planes, such as a coronal plane 202, a sagittal plane 204, and a transverse plane 206, are examples of anatomical orientations. In the illustrated example, the planes 202, 204, 206 extend orthogonal to each other and bisect the subject 50. Yet anatomical orientations can be defined without specifying a predefined location relative to the subject's anatomy (e.g., without indicating a location that bisects the subject 50 or even intersects the subject 50). For example, an anatomical orientation can be a reference plane that is parallel to the coronal plane 202, even though the reference plane does not bisect the subject 50. Thus, as used herein, information that indicates an orientation for a plane having a defined relationship to the anatomy of the subject 50, such as an orientation parallel to a standard anatomical reference plane, is considered to indicate an anatomical orientation.

Anatomical orientations can be defined in many different ways. For example, a superior-inferior axis 212, a medial-lateral axis 214, and an anterior-posterior axis 216, and axes parallel to these axes 212, 214, 216 are additional examples of anatomical orientations. Orientations of these axes can be determined in addition to or as an alternative to determining orientations of anatomical reference planes. Orientations of anatomical reference axes can be calculated from the orientations of anatomical reference planes, and vice versa. In each example where a plane or axis is determined or registered to a spatial position or device, one or more planes, axes, vectors, points, paths, angles, distances, relative or absolute locations, or other representations of an orientation, or a combination thereof, can alternatively be used. In addition, the spatial orientation of surgical trajectory or alignment having a defined position relative to the subject 50 can also be an anatomical orientation.

Figure 3:
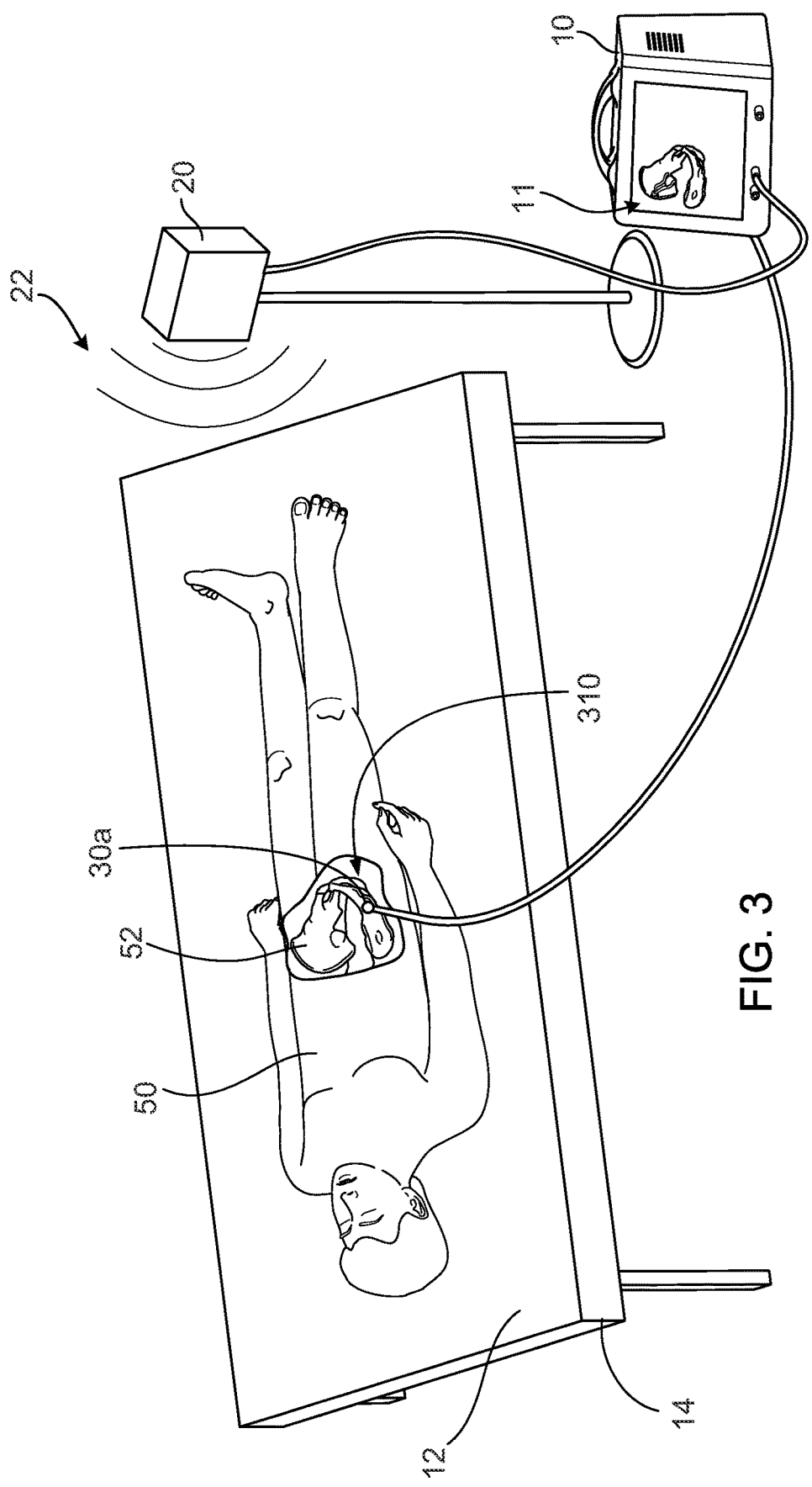
FIGS. 3 to 8 are perspective views illustrating techniques for determining anatomical orientations.

Referring to FIG. 3, a surgeon can use the system 100 to determine anatomical orientations of the subject 50. Anatomical orientations can be determined based on the position of the subject 50 relative to the reference surface 12, which can be the surface of the surgical table 14. The surgeon moves the subject 50 into a known orientation relative to the reference surface 12. For example, the surgeon positions the subject 50 in a standard supine position on the surgical table 14. The subject 50 lies on the surgical table 14 without padding or other obstructions that would alter the position of the subject 50 relative to the reference surface 12. With the subject 50 lying supine on the surgical table 14, the coronal plane 202 (see FIG. 2) of the subject 50 is oriented substantially parallel to the reference surface 12, which can be substantially planar and may be oriented substantially horizontal (e.g., parallel to the ground).

The surgeon dislocates the subject's hip 310 and creates an incision to access the hip. The surgeon couples a magnetic sensor 30a or other reference device to the subject's pelvis 52. The magnetic sensor 30a is coupled such that it moves with the pelvis 52. As a result, the position of the magnetic sensor 30a relative to the pelvis 52 is maintained as the subject 50 moves during surgery. The position of the installed magnetic sensor 30a relative to the pelvis 52 can be maintained throughout an arthroplasty procedure, for example, during preparation of the acetabulum and impaction of the acetabular cup.

In some implementations, the magnetic sensor 30a is attached directly to the pelvis 52. For example, the magnetic sensor 30a can be included in a sensor assembly that includes a threaded housing. The surgeon can use a drill to screw the sensor assembly directly into pelvic bone. The surgeon places the magnetic sensor 30a outside the acetabulum so that the magnetic sensor 30a does not interfere with preparation of the acetabulum and installation of the acetabular implant. As an alternative to directly coupling the magnetic sensor 30a to the pelvis 52, the magnetic sensor 30a can be coupled to the pelvis 52 indirectly through one or more attachment devices such as rods, plates, pins, screws, nails, fasteners, or other connectors.

Figure 4:
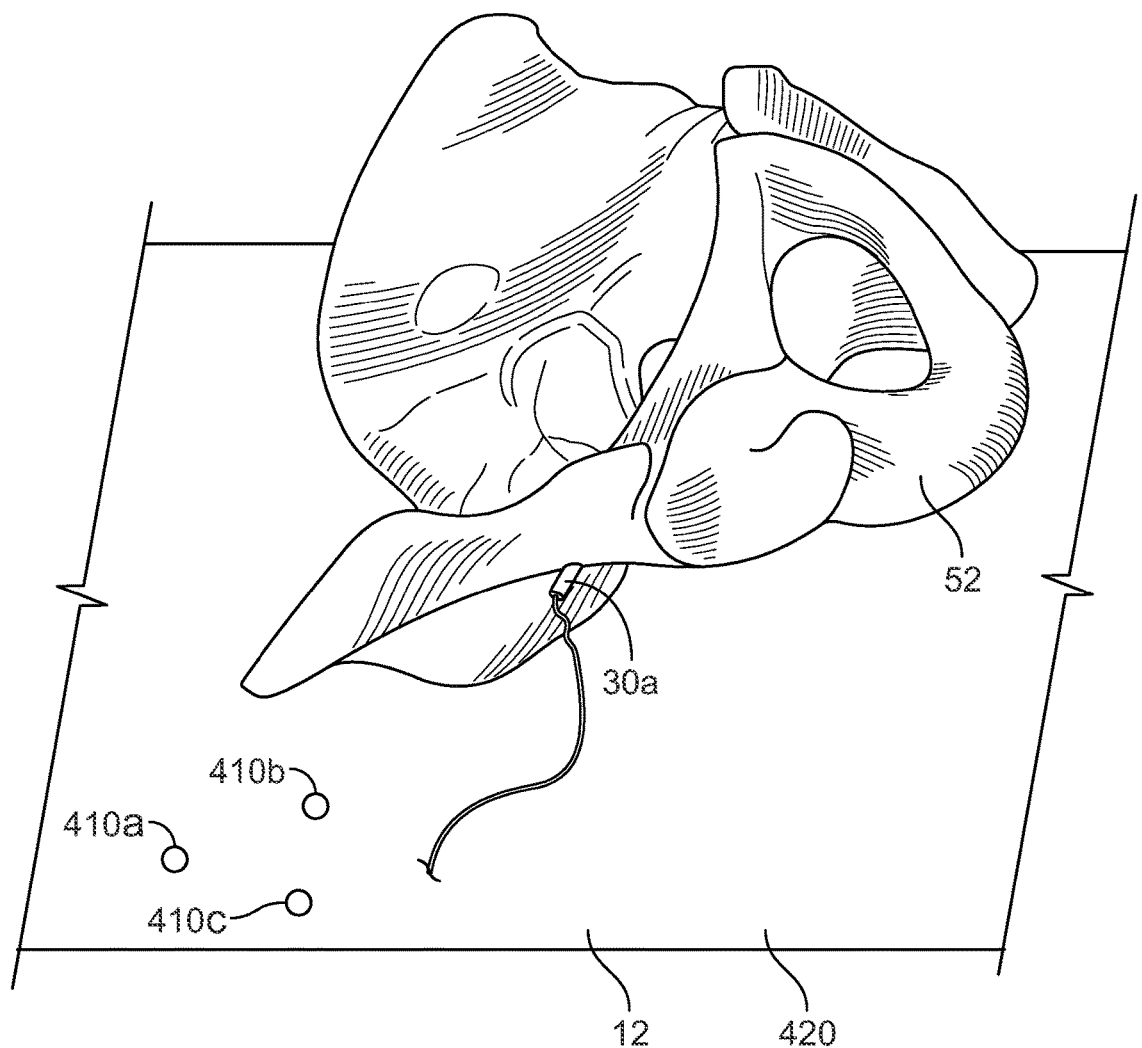

Referring to FIG. 4, the surgeon uses the system 100 to determine an orientation of the reference surface 12. For example, the surgeon determines the orientation that the reference surface 12 extends in a 3D coordinate system. The surgeon uses the probe 70 to measure three different locations 410a-410c (e.g., points) on the reference surface 12. The three locations are not collinear, such that the reference surface 12 can be represented by a plane 420 that intersects the three locations 410a-410c. The magnetic sensor 30b on the probe 70 generates position data that indicates the locations 410a-410c. The position data can indicate, for example, locations relative to the electromagnetic field generator 20 or locations in a coordinate system. The control unit 10 receives the position data and defines the plane 420 through the locations 410a-410c. Because the subject 50 is lying on the reference surface 12, the plane 420 is oriented parallel to the coronal plane 202 of the subject 50. The control unit 10 can determine positions of the magnetic sensor 30a when the locations 410a-410c are measured, permitting the locations 410a-410c and any orientations based on them to be registered to the position of the magnetic sensor 30a. Once the position of the reference surface 12 is determined relative to the magnetic sensor 30a, the subject 50 can be moved from the predetermined orientation relative to the reference surface 12 (e.g., from laying supine on the reference surface 12).

In some implementations, other methods are used to determine the orientation of the reference surface 12. For example, one or more magnetic sensors or other reference devices may be coupled to the reference surface 12, such that a probe is not needed. As an alternative, the orientation of reference surface 12 can have a fixed relationship to the electromagnetic field generator 20 or another element of the system 100. The control unit 10 can determine the orientation of the reference surface 12 by accessing stored data that indicates the predetermined orientation. As another alternative, the probe 70 may be engaged to the reference surface 12 in a known orientation, for example, with a flat side of the probe 70 engaged against the reference surface 12. The orientation of the probe 70 against the reference surface 12 can thus indicate the orientation of the plane 420 or a parallel plane at a single location.

Figure 5:
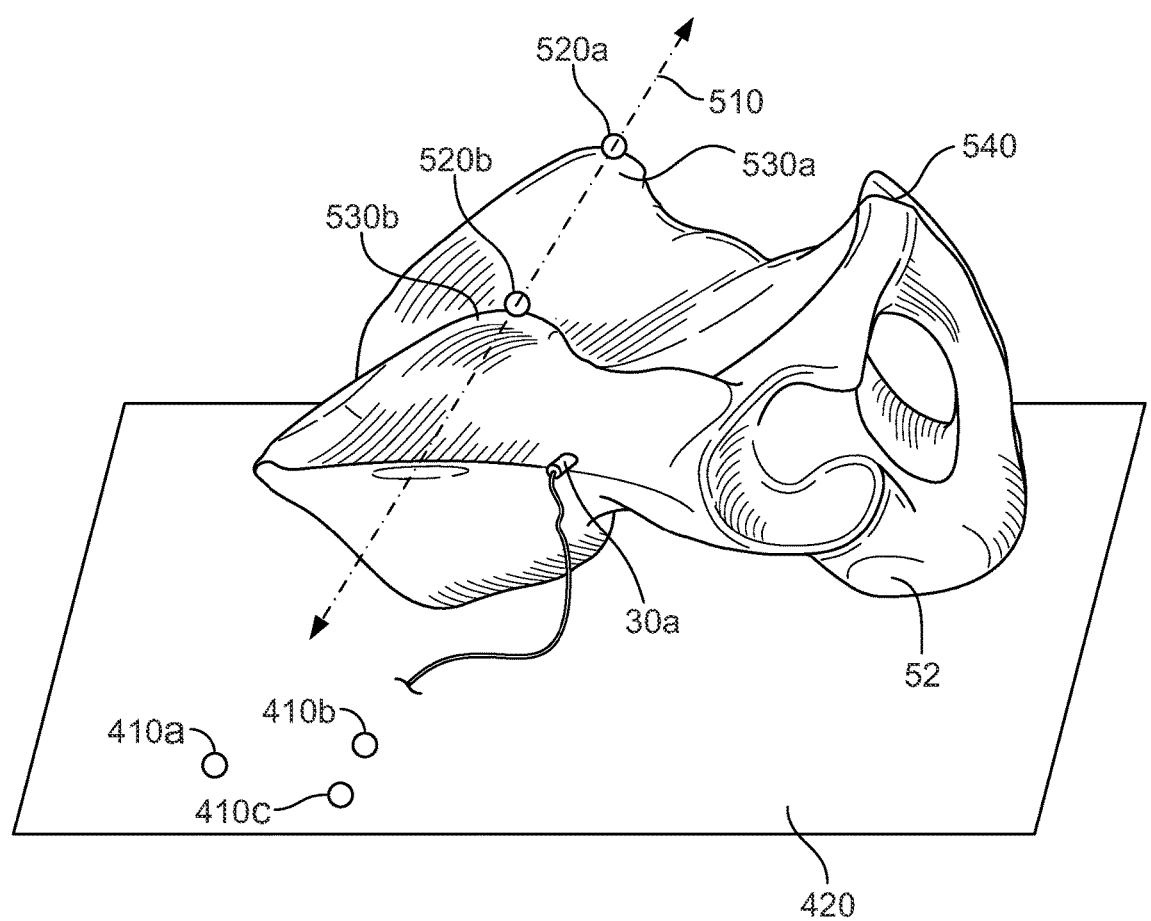

Referring to FIG. 5, the surgeon uses the system 100 to determine a substantially medial-lateral direction of the subject 50, for example, the orientation of a medial-lateral axis 510. The medial-lateral axis 510 is determined based on features of the pelvis 52. For example, the surgeon can use the probe 70 to measure two locations 520a, 520b that correspond to anatomical landmarks of the pelvis 52. The anatomical landmarks can be corresponding features on the right and left sides of the pelvis 52 (e.g., features that are symmetrical across the sagittal plane), such that the anatomical landmarks lie along a medial-lateral axis of the subject 50.

In some implementations, the surgeon contacts the probe end 72 to the skin of the subject 50 to measure the locations 520a, 520b. For example, the surgeon measures the first location 520a such that it corresponds to the left anterior superior spine 530a of the ilium, and the second location 520b such that it corresponds to the right anterior superior spine 530b of the ilium. Typically, the left and right anterior superior spine of the ilium can be easily located through the skin while the subject 50 is supine. Nevertheless, other locations, corresponding to other anatomical landmarks or features of the pelvis 52, can also be measured. As an example, in some implementations, a surgeon locates a pubic symphysis 540 and records the location using the probe 70. The location of the pubic symphysis 540 can be used to determine a pelvic tilt angle, as discussed further below.

The control unit 10 receives position data indicating the locations 520a, 520b and defines the medial-lateral axis 510 through the locations 520a, 520b. The control unit 10 can determine positions of the magnetic sensor 30a when the locations 410a-410c are measured, permitting the locations 520a, 520b and any orientations based on them to be registered to the position of the magnetic sensor 30a and to the plane 420. Because the locations of features of the pelvis 52 are used to define the medial-lateral axis 510, the medial-lateral axis 510 can be determined accurately with respect to the pelvis 52 and the medial-lateral axis 510 has a fixed relationship relative to the magnetic sensor 30a.

In some implementations, the magnetic sensor 30a is attached to the pelvis 52 at an anatomical landmark of the pelvis 52, such as the left or right anterior superior spine of the ilium. As a result, the position of the magnetic sensor 30a defines one of the locations 520a, 520b, and a single measurement can determine the other location 520a, 520b that defines the medial-lateral axis 510.

Figure 6:
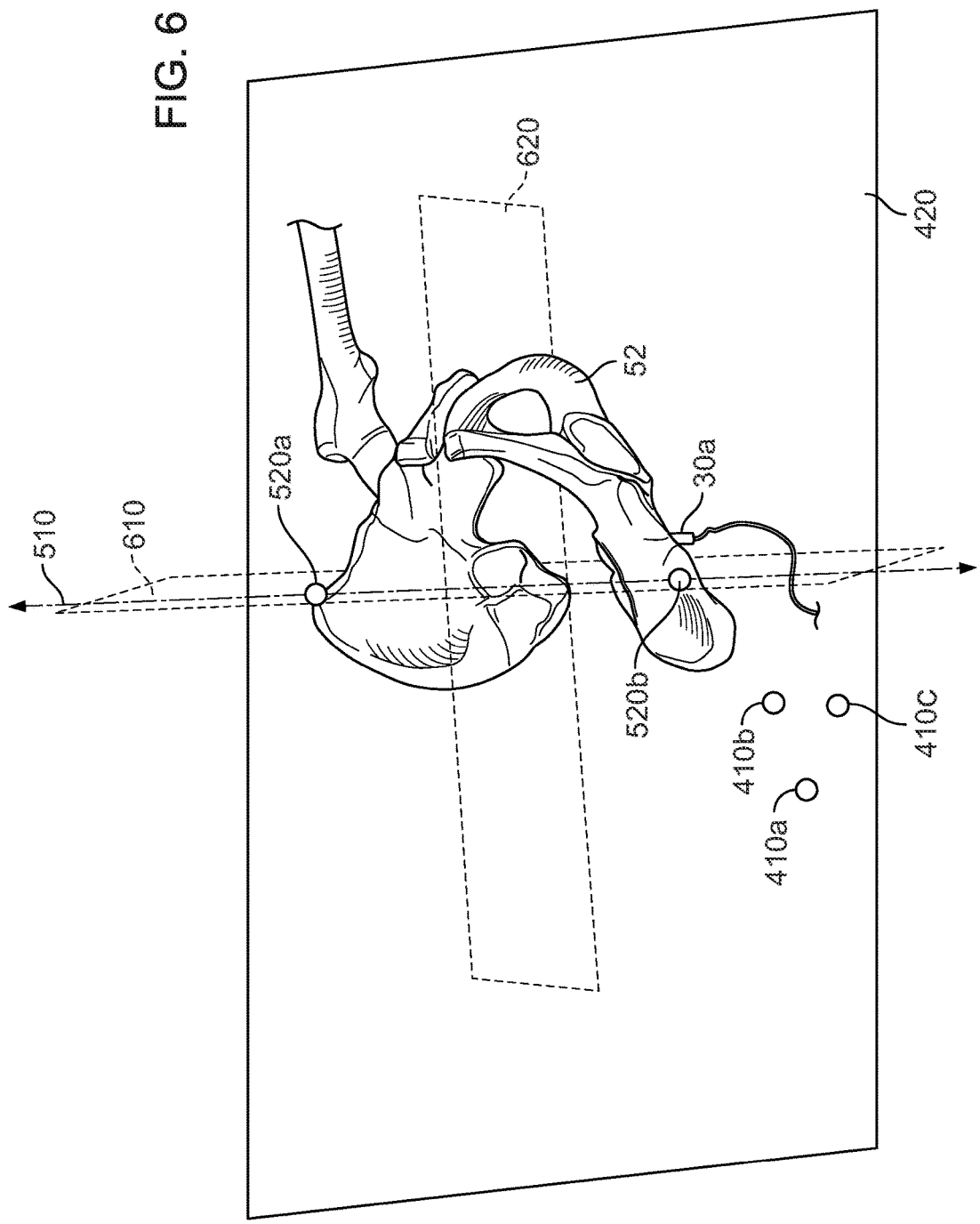

Referring to FIG. 6, the control unit 10 determines orthogonal planes 420, 610, 620. Each of the planes 420, 610, 620 indicates an anatomical orientation of the subject 50. For example, the control unit 10 defines a second plane 610 to be orthogonal to the plane 420 and to include (e.g., extend along) the medial-lateral axis 510. As a result, the plane 610 is oriented parallel to the transverse plane 206 (see FIG. 2) of the subject 50. The control unit 10 defines a third plane 620 to be orthogonal to the plane 420 and the second plane 610, such that the third plane 620 is substantially parallel to the sagittal plane 204 (see FIG. 2) of the subject 50. The control unit 10 can define the third plane 620 at a location in the coordinate system halfway between the locations 520a, 520b, such that the third plane 620 is located to substantially coincide with the sagittal plane 204.

The control unit 10 registers the planes 420, 610, 620 to the position of the magnetic sensor 30a. For example, the control unit 10 determines relative positions between the planes 420, 610, 620 and the magnetic sensor 30a. Because the magnetic sensor 30a moves with the pelvis 52, the relative positions remain constant even as the subject 50 moves. Once the relative positions are determined, the control unit 10 can determine the orientations of the planes 420, 610, 620 for any posture of the subject 50 based on the position of the magnetic sensor 30a.

The control unit 10 can determine the positions of the magnetic sensor 30a and the planes 420, 610, 620 in a common coordinate reference system. The control unit 10 calculates and stores offsets between the positions of the planes 420, 610, 620 and the position of the magnetic sensor 30a. In some implementations, a position of the magnetic sensor 30a and the positions of the planes 420, 610, 620 are all determined in a common coordinate reference frame, for example, a global reference frame. In some implementations, the positions of the planes 420, 610, 620 are determined in a coordinate reference frame defined relative to magnetic sensor 30a. For example, the coordinate system may be defined such that the position of the magnetic sensor 30a represents the origin in the coordinate system, regardless of how the magnetic sensor 30a moves in actual 3D space.

Figure 7:
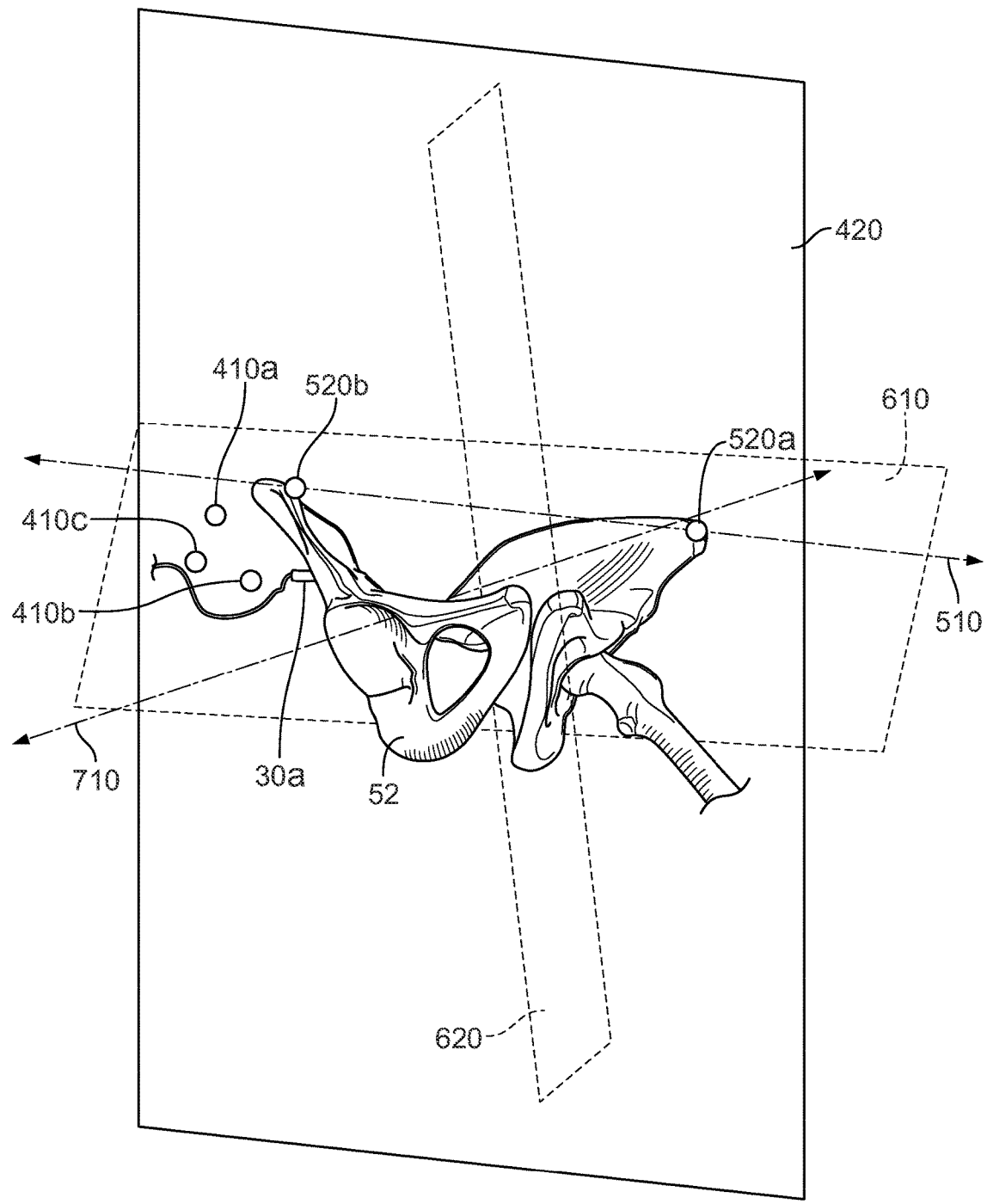

Referring to FIG. 7, a surgical trajectory is defined relative to the pelvis 52. For example, the surgical trajectory can be an impaction axis 710 along which reaming of the acetabulum and/or impaction of an acetabular cup implant can occur. The surgeon can input a desired anteversion angle and a desired inclination angle for the impaction axis 710 to the control unit 10. The control unit 10 then determines the orientation of the impaction axis 710 (e.g., determines the spatial direction that the impaction axis 710 extends in a 3D coordinate reference system) such that the impaction axis 710 has the desired angles relative to the planes 420, 610, 620. The control unit 10 can register the orientation of the impaction axis 710 relative to the position of the magnetic sensor 30a, in addition to or as an alternative to registering the orientations of the planes 420, 610, 620.

Because the control unit 10 tracks movement of the pelvis 52 based on the position of the magnetic sensor 30a, the control unit 10 can maintain the relative orientation between the impaction axis 710 and the pelvis 52. As the position of the magnetic sensor 30c changes in in the operating theater, for example, as the detected position of the magnetic sensor 30c changes in a global coordinate reference system, the control unit 10 can adjust the orientation of the impaction axis 710 as defined in the operating theater to maintain a consistent position relative to the pelvis 52. As a result, the surgeon can move the subject 50 from a supine position to, for example, a lateral position in which the subject 50 is lying on her side during surgery. Thus the surgeon is not limited to a direct anterior approach. The surgeon may move the subject 50 into multiple different positions during the procedure, including moving the subject 50 off of the reference surface 12, and still use the system 100 to determine the orientation of the impaction axis 710 relative to the pelvis 52. The surgeon can also use the system to define other surgical trajectories relative to the pelvis 52 after the subject 50 is moved.

Figure 8:
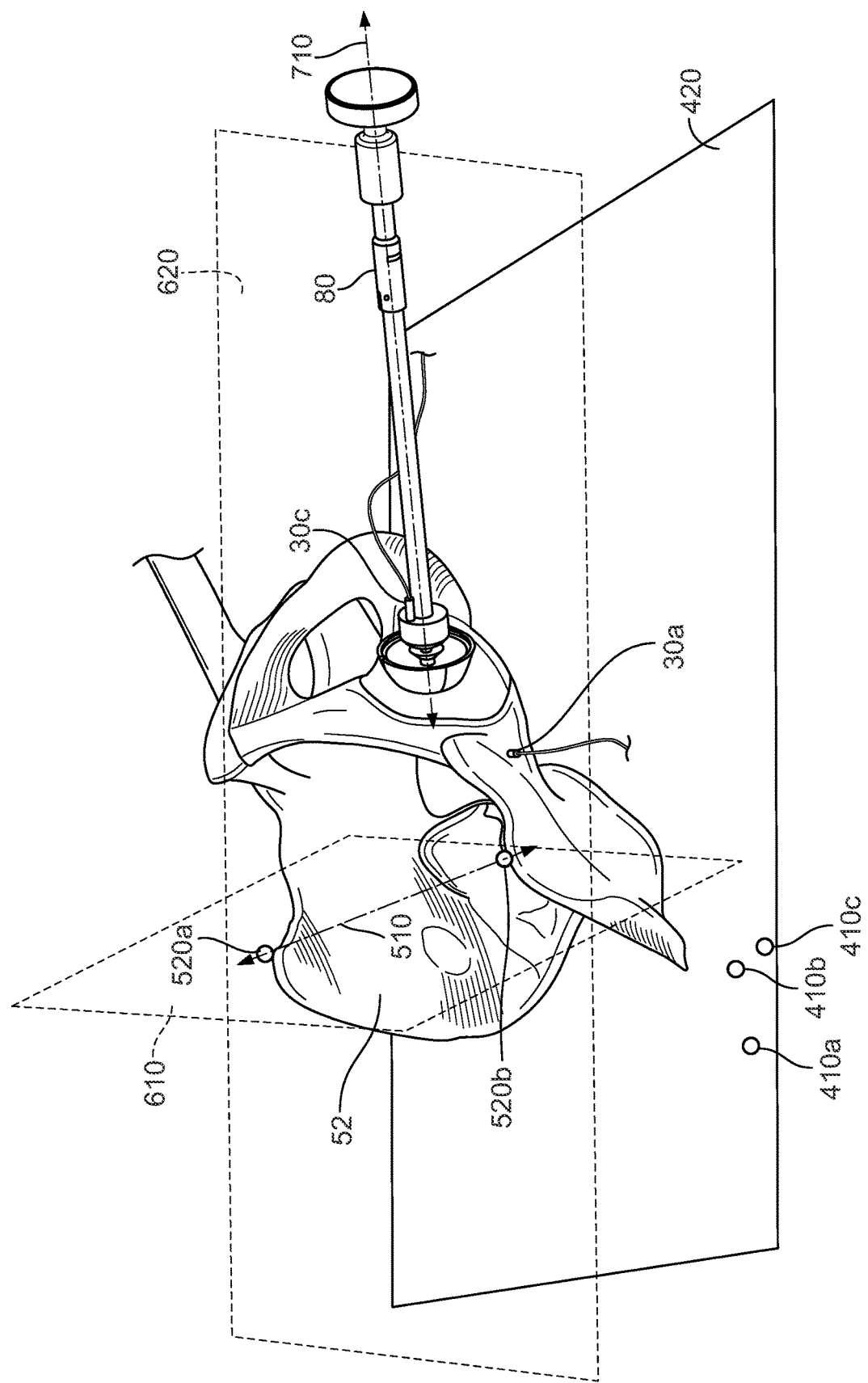

Referring to FIG. 8, the surgeon orients the surgical tool 80 relative to the pelvis 52, guided by the system 100. The control unit 10 receives position data from the magnetic sensor 30c, which is attached to the surgical tool 80. The control unit 10 uses the position data to determine the position of surgical tool 80 relative to the impaction axis 710. The control unit 10 provides feedback to the surgeon about deviation of the surgical tool 80 from the orientation of the impaction axis 710. The control unit 10 can also confirm that the orientation of the surgical tool 80 is acceptable, for example, when the surgical tool 80 is determined to be oriented within a predetermined tolerance of the orientation of the impaction axis 710.

In some implementations, the control unit 10 outputs on a user interface one or more elements, such as an element representing the angle of the surgical tool 80 relative to a surgical alignment, one or more elements representing acceptable positions of the surgical tool 80 relative to the surgical alignment, one or more elements representing unacceptable positions of the surgical tool 80 relative to the surgical alignment, a numeric indication of the angle of the surgical tool 80 relative to anatomical axes, an element indicating that the current position of the surgical tool 80 is acceptable, and an element indicating that the current position of the surgical tool 80 is unacceptable.

To facilitate determining the position of the surgical tool 80, the magnetic sensor 30c can be attached at a predetermined orientation and/or location of the surgical tool 80, and thus can have a known positional offset from, for example, an end or shaft of the surgical tool 80. Alternatively, offsets between the magnetic sensor 30c and the surgical tool 80 can be determined using a sensor calibration process after the magnetic sensor 30c is attached.

In some implementations, the control unit 10 does not indicate the particular location that the surgical trajectory intersects the pelvis. A surgeon can manually locate an end of the surgical tool 80 at the center of the acetabulum and position the surgical tool 80 in the orientation indicated by the control unit 10.

As an alternative, the control unit 10 receives additional information that is used to define a particular location of the impaction axis 710, in addition to the orientation determined relative to the planes 420, 610, 620. For example, the control unit 10 can access information about a central location of the acetabulum or a center of motion of the hip 320, and use the information to define the location of the impaction axis 710. For example, the impaction axis 710 may be defined through the center of motion of the hip or central location of the acetabulum. The control unit 10 may output data that indicates the location and orientation of the impaction axis 710 relative to an image or other representation of a pelvis. In addition to displaying the impaction axis 710 (and deviations of surgical tools from the impaction axis 710), the control unit 10 may indicate the location and orientation of surgical tools with respect to a representation of a pelvis. Once the location of the impaction axis 710 is fully determined, the control unit 10 can determine and display additional data, for example, a depth to which the acetabulum has been reamed and/or an extent of impaction of an acetabular shell into a prepared (e.g., reamed) acetabulum.

Referring to FIGS. 9A and 9B, in some implementations, a pelvic tilt angle, $\Theta$, is used to adjust the orientation of the plane 420. The pelvic tilt angle, $\Theta$, can represent a difference between the orientation of the pelvis 52 of a particular subject 50 and a typical or expected orientation relative to the reference surface 12 or the coronal plane 202 of the subject 50. The control unit 10 can use the pelvic tilt angle, $\Theta$, to accurately determine the anatomical alignment of the pelvis 52 relative to the reference surface 12. The pelvic tilt angle, $\Theta$, for a particular subject 50 can be determined by a physician and the value can be entered to the control unit 10 or another system. Various measurement techniques can be used to determine the pelvic tilt angle, $\Theta$.

In some instances, soft tissue or other obstructions may cause the orientation of the subject 50 to vary from a position in which the coronal plane 202 of the subject is substantially parallel to the reference surface 12. For example, the hip 320 may be raised above a shoulder 920 of the subject 50 while lying on a horizontal reference surface.

To determine the pelvic tilt angle, $\Theta$, for example, a pre-operative x-ray image 900 of the subject 50 can be acquired while the subject 50 lies supine on a surface 902. The image 900 can show a lateral view of the subject 50, and a line 905 can be defined between the hip 320 and a shoulder 920 of the subject 50. The angle between the line 905 and the surface 902 can be defined as the pelvic tilt angle, $\Theta$.

As shown in FIG. 9B, the orientation of the plane 420 can be adjusted by the amount of the pelvic tilt angle, $\Theta$, to define an adjusted plane 930. Because the adjusted plane 930 is defined using the pelvic tilt angle, $\Theta$, the adjusted plane 930 represents the orientation of the coronal plane 202 of the subject 50 more closely than the plane 420, which represents the orientation of the reference surface 12. To define the adjusted plane 930, the control unit 10 accesses data that indicates the pelvic tilt angle, $\Theta$, for example, input from the surgeon. The control unit 10 defines the adjusted plane 930 at the angular offset of the pelvic tilt angle, $\Theta$, relative to the determined orientation of the reference surface 12.

Other techniques for determining a pelvic tilt angle can also be used. For example, the surgeon can determine or estimate a pelvic tilt angle based on features of the pelvis 52. The surgeon can identify features of the pelvis 52 on a radiograph and determine a pelvic tilt angle using, for example, relative positions of the features, distances along the pelvis, or ratios of the distances. Lateral and/or anterioposterior radiographs can be used. In addition or as an alternative to using the pelvic tilt angle, $\Theta$, illustrated, one or more other pelvic tilt angles, such as an angle indicating a difference between a typical orientation of a pelvis relative to a coronal plane and the actual orientation of the pelvis 52 relative to the coronal plane 202 of the subject 50, can be used to define the orientation of the adjusted plane 930.

In some implementations, pelvic tilt can be measured using the locations of the anterior superior iliac spine and the pubic symphysis. An anterior pelvic plane may be defined through the left anterior superior spine of the ilium, the right anterior superior spine of the ilium, and the pelvic symphysis. The angle between the anterior pelvic plane and the plane 420 can be used as the pelvic tilt angle. The pubic symphysis can be palpated and registered by the surgeon like the anterior superior iliac spine, for example, using the probe 70. The control unit 10 can record data indicating the locations of the left anterior superior spine of the ilium, the right anterior superior spine of the ilium, and the pelvic symphysis. The control unit 10 may then define the anterior pelvic plane and determine the pelvic tilt angle as the angle between the anterior pelvic plane and the plane 420. In some implementations, when the pelvic tilt angle is determined in this manner, the need for a pre-operative x-ray image to determine pelvic tilt can be eliminated.

In some implementations, the control unit 10 can access x-ray image data for the subject 50 and calculate the value of the pelvic tilt angle, $\Theta$. For example, the surgeon can indicate the locations of the hip 320 and the shoulder 920 on the x-ray image 900, or can indicate locations of particular features of the pelvis 52, and the control unit 10 can determine the appropriate pelvic tilt angle, $\Theta$.

Figure 10:
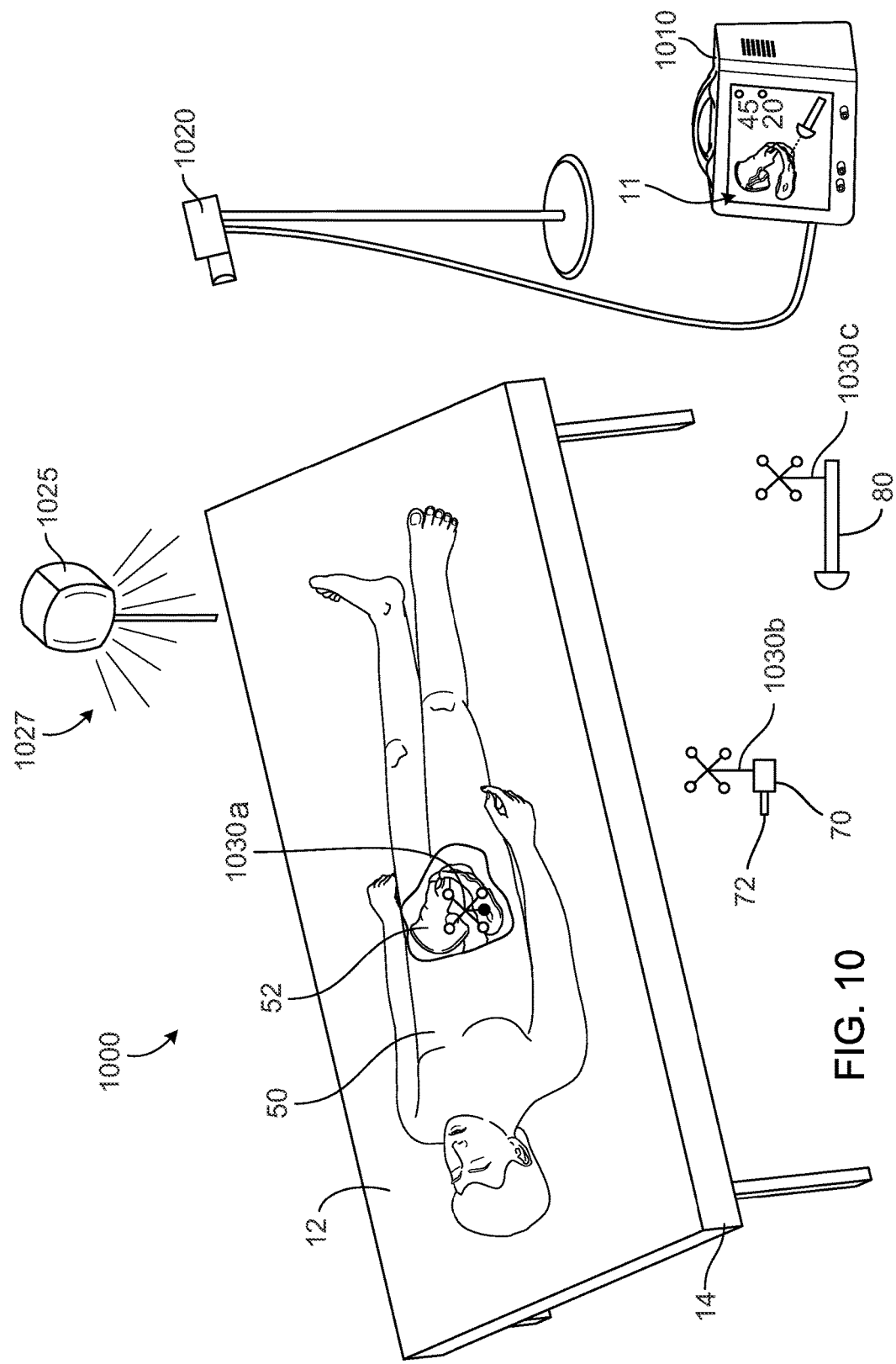
FIG. 10 is a diagram of an example of a system that can determine anatomical orientations.

Referring to FIG. 10, a spatial tracking system 1000 can be used to determine anatomical orientations using optical tracking techniques. An operator can use the spatial tracking system 1000 to determine anatomical orientations in the same manner as described for the system 100.

The spatial tracking system 1000 includes a control unit 1010, a camera 1020, a light source 1025, and two or more reference devices such as fiducials 1030a-1030c. One of the fiducials 1030a is configured to move with the pelvis 52 of the subject 50, for example, by attaching to the pelvis 52 at a fixed position. A second fiducial 1030b is attached to the probe 70, and a third fiducial 1030c is attached to the surgical tool 80. The light source 1025 directs light, for example, infrared light 1027, into the operating theater, and the camera 1020 detects reflections of the infrared light 1027 from the fiducials 1030a-1030c. The control unit 1010 receives data from the camera 1020, and determines positions of the fiducials 1030a-1030c. For example, the control unit 1010 can use triangulation or other techniques to determine positions relative to the camera 1020, which can remain in a fixed position, or to determine positions of the fiducials 1030a-1030c relative to each other. The control unit 1010 registers anatomical orientations to the fiducial 1030a, permitting the anatomical orientations to be defined in the operating theater as the pelvis 52 moves.

Other spatial tracking techniques and systems can also be used. For example, radiofrequency transmissions can be used to determine spatial positions. A radiofrequency sensor, for example, a sensor that includes one or more radiofrequency antennas, can be used as a reference device. A radiofrequency transmitter can transmit patterns of radiofrequency transmissions that are detected by the radiofrequency sensor. When the radiofrequency sensor detects sufficient radiofrequency energy, the radiofrequency sensor produces signals indicating the position of the radiofrequency sensor relative to the radiofrequency transmitter.

In general, a system for spatial tracking can include a first reference device that can be configured to move with a pelvis. The system can include one or more second reference devices, for example, that can be configured to move with one or more probes or one or more surgical tools. The first reference device and the one or more second reference devices can each include, for example, a magnetic sensor, a fiducial, or a radiofrequency sensor. A communication module can be configured to communicate with the first reference device and the one or more second reference devices to permit the positions of the first reference device and the one or more second reference devices to be tracked. For example, the communication module can include, for example, an electromagnetic field generator, a camera, or a radiofrequency transmitter. A control unit can be operably coupled to the communication module, for example, to send control signals and/or receive data about positions of the first reference device and the one or more second reference devices. In some implementations, the control unit receives information about positions of the first reference device and the one or more second reference devices from the first reference device and the one or more second reference devices.

Figure 11:
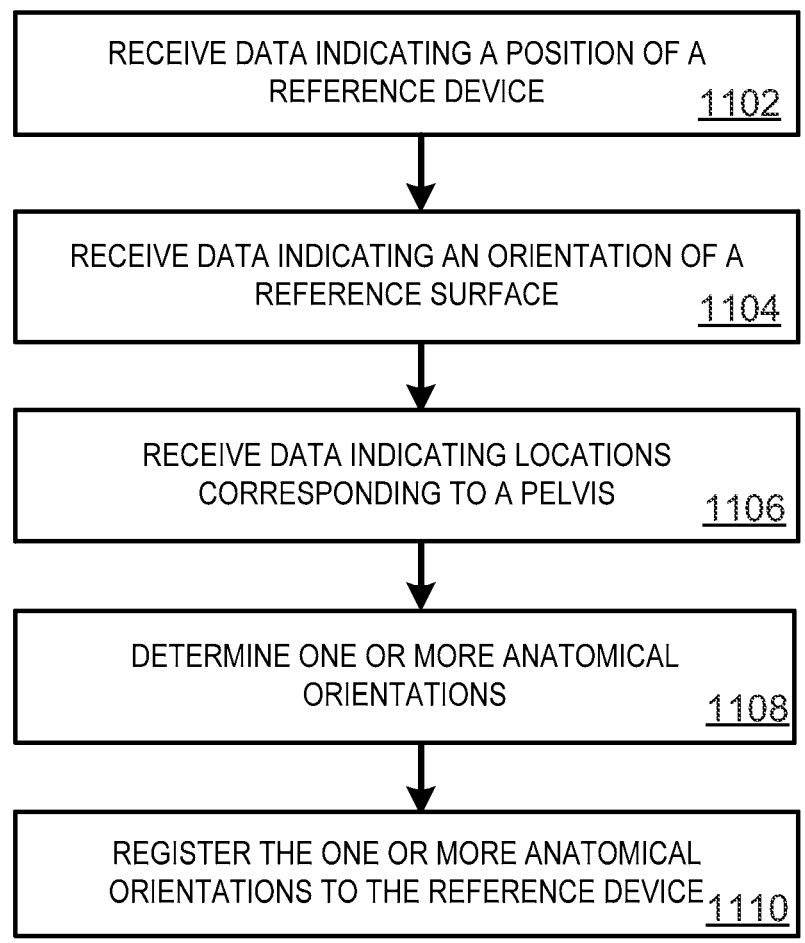
FIGS. 11 to 13 are flow diagrams illustrating processes for determining anatomical orientations.

Referring to FIG. 11, a process 1100 can be used to determine anatomical orientations of a subject. The process 1100 can be performed by, for example, a control unit such as one of the control units 10, 1010 described above.

Data indicating a position of a reference device is received (1102). The data indicates the position of the reference device while the reference device is configured to move with, for example, a pelvis of a subject. For example, the reference device can be directly or indirectly attached to bone of the pelvis or some other anatomical feature of the subject.

The reference device can include one or more of, for example, a magnetic sensor, a fiducial, and an RF sensor. Thus receiving the data can include receiving data from a magnetic sensor, receiving data from an RF sensor, or receiving data indicating a position of a fiducial. The data can indicate a location and an orientation of the reference device in a three-dimensional coordinate system.

Data indicating an orientation of a reference surface is received (1104). The reference surface can be, for example, a substantially planar surface such as a surface of a surgical table or a substantially vertical surface, such as a wall. The reference surface can be oriented horizontally, for example, substantially parallel to the ground, or in another orientation.

The data can indicate locations corresponding to the reference surface. For example, the data can indicate locations measured while a measurement device, such as a probe coupled to a second reference device, is engaged with the reference surface. The data indicating the orientation of the reference surface can include data identifying locations along the reference surface, for example, locations on the reference surface. The data can indicate at least three locations that are not collinear. The locations can be represented as points in a three-dimensional coordinate system.

Data indicating locations corresponding to a pelvis is received (1106). The data can indicate extracutaneously measured locations, for example, locations of a probe when the probe contacts a subject's skin. The locations can be indicated as points, vectors, or other representations. The locations can correspond to anatomical features of the pelvis that are oriented along a medial-lateral direction of the subject. For example, the locations can correspond to the left anterior superior spine of the ilium and the right anterior superior spine of the ilium.

One or more anatomical orientations are determined (1108). The anatomical orientations are determined based on the locations corresponding to the reference surface and the locations corresponding to the pelvis. For example, the one or more anatomical orientations can be spatially determined in a 3D coordinate system. When the received data indicates at least three locations on a substantially planar surface, an orientation of a coronal plane of the subject can be determined based on the at least three locations. When the received data indicates at least two locations on the pelvis that are located substantially along a medial-lateral axis, an orientation that extends along a substantially medial-lateral direction of the subject can be determined based on the at least two locations on the pelvis. Orientations of planes that are substantially parallel to a coronal plane, a transverse plane, and a sagittal plane of the subject can be determined. In addition, or as an alternative, one or more surgical trajectories can also be determined.

To determine an anatomical orientation, information indicating a pelvic tilt angle can be received. An orientation of a coronal plane of the subject can be determined to have an offset equal to the pelvic tilt angle from the orientation of the reference surface.

The one or more anatomical orientations are registered to the reference device (1110). For example, the relative positions of the one or more anatomical orientations and the position of the reference device can be determined. The one or more anatomical orientations and the reference device can be registered in a common coordinate reference frame.

In some implementations, the process 1100 includes determining a surgical trajectory. The surgical trajectory can be a trajectory for arthroplasty of the pelvis. For example, the surgical trajectory can be an axis for reaming an acetabulum or an acetabular impaction axis for impacting an acetabular implant. The surgical trajectory can be defined in a coordinate reference system in which the reference device is registered. The orientation of the surgical trajectory relative to the subject can be determined based on the one or more anatomical orientations. The surgical trajectory can have a predetermined or operator-defined inclination angle and anteversion angle relative to the one or more anatomical orientations.

In some implementations, the process 1100 includes determining a position of a tool relative to the surgical trajectory based on a position of the reference device. The tool can be, for example, a reamer or an impactor. The process 1100 includes outputting data indicating the orientation of the tool relative to the surgical trajectory.

In some implementations, the data indicating the position of the reference device indicates a position of the reference device corresponding to a first position of the subject. For example, in the first position the subject can lie supine on the reference surface. The data indicating the position of the reference device can also indicate a position of the reference device corresponding to a second position of the subject that is different from the first position. For example, the subject can be lying on her side.

The anatomical orientations can be adjusted based on the position of the reference device corresponding to the second position of the subject. For example, the anatomical orientations can be adjusted in a global coordinate reference system. As the position of the reference device is changes, the anatomical orientations can be adjusted to reflect corresponding changes in position. A position of a surgical trajectory in a coordinate system can be determined relative to the adjusted anatomical orientations, and a position of a tool can be determined relative to the surgical trajectory.

Figure 12:
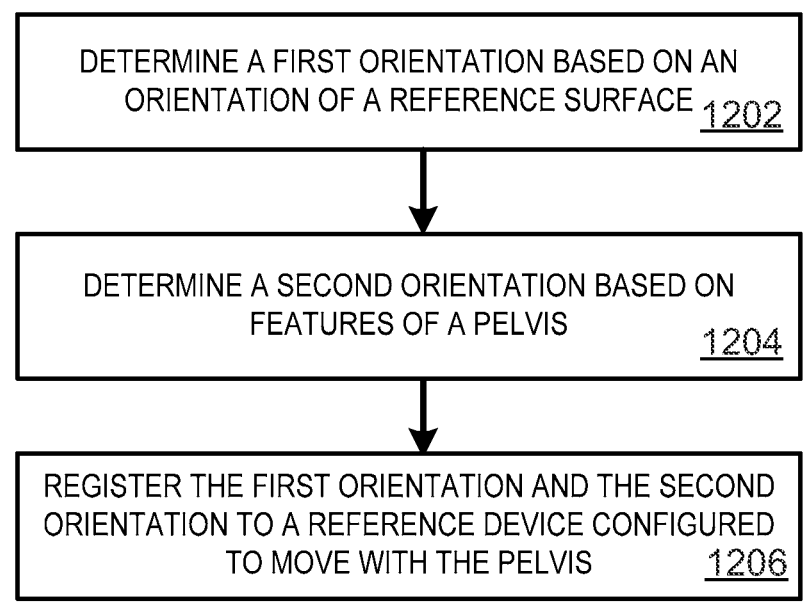

Referring to FIG. 12, a process 1200 can be used to determine anatomical orientations of a subject. The process 1200 can be performed by, for example, a control unit such as one of the control units 10, 1010 described above.

A first orientation is determined based on an orientation of a reference surface (1202). The first orientation can be determined (e.g., the spatial orientation can be determined in a 3D coordinate reference system) based on data indicating three or more locations on the reference surface. Determining the first orientation can include determining an orientation of a coronal plane for the subject. In some implementations, the first orientation is determined based on the orientation of the reference surface and a pelvic tilt angle.

A second orientation is determined based on features of a pelvis (1204). The second orientation can extend along a substantially medial-lateral direction of the subject. The second orientation can be determined (e.g., the spatial orientation can be determined in a 3D coordinate reference system) based on features of a pelvis of the subject.

Determining the second orientation can include determining the orientation of an axis that extends along the substantially medial-lateral direction. Determining the second orientation can include determining an orientation of a transverse plane of the subject. The second orientation can be determined based on data that indicates a location corresponding to the left anterior superior spine of the ilium and data that indicates a location corresponding to the right anterior superior spine of the ilium. The second orientation can be determined based on data indicating positions of a probe while the probe is engaged with skin of the subject that covers the pelvis, where the probe is coupled to a fiducial or a magnetic field sensor.

The first orientation and the second orientation are registered to a reference device that is configured to move with the pelvis (1206). For example, the relative position of the reference device and the first orientation and the second orientation can be determined and stored in a data storage device. The position of the reference device and the first orientation and the second orientation can be determined in a common coordinate reference system. The position of the reference device can be determined based on data generated by a magnetic sensor of the reference device. The position of the reference device can be determined based on data indicating the position of a fiducial of the reference device.

The process 1200 can include determining a third orientation that extends perpendicular to the first orientation and the second orientation, registering the third orientation to the position of the reference device. Determining the third orientation can include determining an orientation of a sagittal plane for the subject.

The process 1200 can include determining a surgical trajectory using the first orientation, the second orientation, and the orientation of the reference device. To determine the surgical trajectory, the surgical trajectory can be defined at a predetermined inclination angle and a predetermined anteversion angle. A tool can be aligned relative to the surgical trajectory using the reference device. For example, the orientation of the surgical trajectory can be determined in an operating theater based on the position of the reference device in the operating theater.

In some implementations, the first orientation and the second orientation are registered to a position of the reference device while the subject is positioned in a first position that is supine relative to the reference surface. The process 1200 can include determining an updated position of the reference device, where the updated position corresponds to a second position of the subject that is not a supine position relative to the reference surface. Updated orientations, having the same relative orientation to the subject as the first orientation and the second orientation, can be determined based on the updated position of the reference device.

Figure 13:
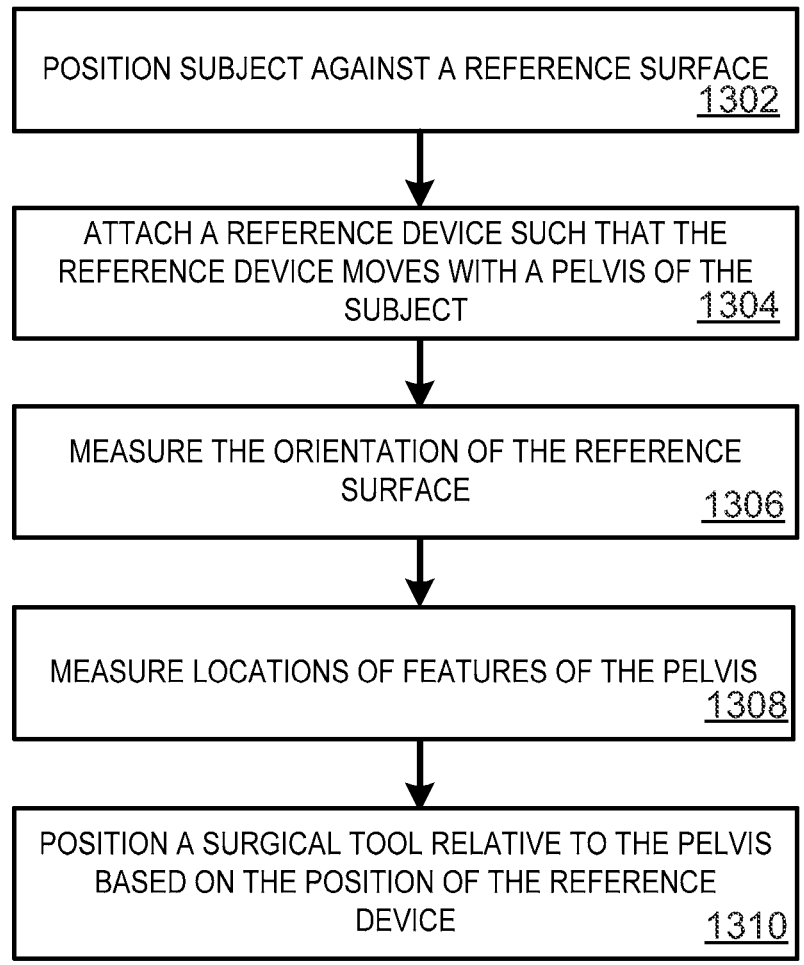

Referring to FIG. 13, a process 1300 can be performed by a surgeon to orient a surgical tool relative to a pelvis of a subject.

The subject is positioned against a reference surface (1302). The subject can be positioned in a predetermined orientation relative to the reference surface. For example, the surgeon can position the subject supine on the surface of a surgical table, which can be substantially planar.

A reference device is attached to the pelvis such that the reference device moves with the pelvis (1304). For example, the reference device can be attached to the pelvis at a fixed position. The reference device can include a magnetic sensor, a fiducial, or a radiofrequency sensor.

The orientation of the reference surface is measured (1306). For example, the surgeon engages a probe against the reference surface. The probe can be engaged with the reference surface at three different, non-collinear locations while the subject is supine on the surgical table. A spatial tracking system can be used to determine the position of the reference device while the subject is supine on the reference surface.

Locations of features of the pelvis are measured (1308). For example, the surgeon can engage the probe to two locations corresponding to features of the pelvis. The probe can be engaged with extracutaneous locations corresponding to a left anterior superior spine of the ilium and a right anterior superior spine of the ilium of the pelvis.

A surgical tool is positioned relative to the pelvis based on a position of the reference device (1310). The surgical tool can be aligned along a surgical trajectory defined using the orientation of the reference surface and the locations of the features of the pelvis. The surgical trajectory can be an impaction axis having a fixed orientation relative to the reference device. The surgical trajectory can be defined at a predetermined anteversion angle and a predetermined inclination angle relative to anatomical reference orientations determined using the orientations of the reference surface and the locations of the features of the pelvis.

In some implementations, the subject is moved from the supine position to a lateral position, and the surgical tool is aligned relative to the surgical trajectory while the subject is in the lateral position.

In some implementations, the control unit 10 or the control unit 1010 includes one or more processing devices and one or more data storage devices. The one or more data storage devices store instructions that, when executed by the one or more processing devices, cause the one or more processing devices to perform the operations of the process 1100, the process 1200, or the other operations described herein. In some implementations, a non-transitory computer-readable medium stores instructions that are operable, when executed by one or more processing devices, to cause the one or more processing devices to perform the operations of the process 1100, the process 1200, or other operations described herein.

Embodiments and all of the functional operations described in this specification may be implemented in digital electronic circuitry, or in computer software, firmware, or hardware, including the structures disclosed in this specification and their structural equivalents, or in combinations of one or more of them. Implementations can include one or more computer program products, i.e., one or more modules of computer program instructions encoded on a computer-readable medium for execution by, or to control the operation of, data processing apparatus. The computer-readable medium may be a non-transitory computer readable storage medium, a machine-readable storage device, a machine-readable storage substrate, a memory device, a composition of matter effecting a machine-readable propagated signal, or a combination of one or more of them. The term "data processing apparatus" encompasses all apparatus, devices, and machines for processing data, including by way of example a programmable processor, a computer, or multiple processors or computers. The apparatus may include, in addition to hardware, code that creates an execution environment for the computer program in question, e.g., code that constitutes processor firmware, a protocol stack, a database management system, an operating system, or a combination of one or more of them. A propagated signal is an artificially generated signal, e.g., a machine-generated electrical, optical, or electromagnetic signal that is generated to encode information for transmission to suitable receiver apparatus.

A computer program (also known as a program, software, software application, script, or code) may be written in any form of programming language, including compiled or interpreted languages, and it may be deployed in any form, including as a stand-alone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry, e.g., an FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing instructions and one or more memory devices for storing instructions and data. Generally, a computer will also include, or be operatively coupled to receive data from or transfer data to, or both, one or more mass storage devices for storing data, e.g., magnetic, magneto-optical disks, or optical disks. However, a computer need not have such devices. Moreover, a computer may be embedded in another device, e.g., a tablet computer, a mobile telephone, a personal digital assistant (PDA), a mobile audio player, a Global Positioning System (GPS) receiver, to name just a few. Computer-readable media suitable for storing computer program instructions and data include all forms of non-volatile memory, media, and memory devices, including by way of example semiconductor memory devices, e.g., EPROM, EEPROM, and flash memory devices; magnetic disks, e.g., internal hard disks or removable disks; magneto-optical disks; and CD-ROM and DVD-ROM disks. The processor and the memory may be supplemented by, or incorporated in, special purpose logic circuitry.

To provide for interaction with a user, the techniques described herein can be implemented on a computer having a display device, e.g., a CRT (cathode ray tube) or LCD (liquid crystal display) monitor, for displaying information to the user and a keyboard and a pointing device, e.g., a mouse or a trackball, by which the user may provide input to the computer. Other kinds of devices may be used to provide for interaction with a user as well; for example, feedback provided to the user may be any form of sensory feedback, e.g., visual feedback, auditory feedback, or tactile feedback; and input from the user may be received in any form, including acoustic, speech, or tactile input.

The techniques described herein can be implemented in a computing system that includes a back end component, e.g., as a data server, or that includes a middleware component, e.g., an application server, or that includes a front end component, e.g., a client computer having a graphical user interface or a Web browser through which a user may interact with an implementation of the invention, or any combination of one or more such back end, middleware, or front end components. The components of the system may be interconnected by any form or medium of digital data communication, e.g., a communication network. Examples of communication networks include a local area network ("LAN") and a wide area network ("WAN"), e.g., the Internet.

The computing system may include clients and servers. A client and server are generally remote from each other and typically interact through a communication network. The relationship of client and server arises by virtue of computer programs running on the respective computers and having a client-server relationship to each other.

While this specification contains many specifics, these should not be construed as limitations on the scope of the invention or of what may be claimed, but rather as descriptions of features specific to particular implementations. Certain features that are described in this specification in the context of separate implementations may also be implemented in combination in a single implementation. Conversely, various features that are described in the context of a single embodiment may also be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a sub combination.

Similarly, while operations are depicted in the drawings in a particular order, this should not be understood as requiring that such operations be performed in the particular order shown or in sequential order, or that all illustrated operations be performed, to achieve desirable results. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products.

A number of implementations have been described. Nevertheless, it will be understood that various modifications may be made without departing from the spirit and scope of the disclosure. The techniques described above can be used for other aspects of hip arthroplasty, surgeries involving the pelvis other than hip arthroplasty, and procedures other than arthroplasty. The same techniques can be used to determine anatomical orientations relative to other portions of the anatomy, for example, bones other than the pelvis. A reference device can be attached to different portion of a subject's anatomy, and anatomical orientations can be determined relative to that portion of the subject's anatomy. Accordingly, other implementations are within the scope of the following claims.

What is claimed is:

1. An apparatus comprising:
   one or more processing devices; and
   one or more data storage devices storing instructions that are operable, when executed by the one or more processing devices, to cause the one or more processing devices to perform operations comprising:
   receiving data indicating a position of a reference device configured to move with a pelvis of a subject, wherein the indicated position is a position of the reference device while the subject is in an expected posture with respect to a substantially planar reference surface;
   receiving data indicating at least three locations on the substantially planar reference surface while the subject is in the expected posture with respect to the substantially planar reference surface;
   receiving data indicating locations on the pelvis;
   determining a first anatomical orientation of the subject based on the data indicating the at least three locations on the substantially planar reference surface;
   determining a second anatomical orientation that extends along a substantially medial-lateral direction based on the data indicating the locations on the pelvis;
   registering the first anatomical orientation and the second anatomical orientation to the reference device;
   determining a position of a surgical tool relative to the subject using the registered first anatomical orientation and the registered second anatomical orientation; and
   providing, for output on a display in communication with the apparatus, an indication of the determined position of the surgical tool relative to the subject.

2. The apparatus of claim 1, wherein the operations further comprise:
   determining a surgical trajectory based on the first anatomical orientation and the second anatomical orientation;
   determining a position of a tool relative to the surgical trajectory based on a position of the reference device; and
   outputting data indicating the position of the tool relative to the surgical trajectory.

3. The apparatus of claim 2, wherein determining the surgical trajectory based on the first anatomical orientation and the second anatomical orientation comprises determining an orientation at a predetermined inclination angle and a predetermined anteversion angle relative to the first anatomical orientation and the second anatomical orientation.

4. The apparatus of claim 1, wherein the operations further comprise:
   determining a third anatomical orientation of the subject that is orthogonal to the first anatomical orientation and the second anatomical orientation; and
   registering the third anatomical orientation to the reference device that is configured to move with the pelvis.

5. The apparatus of claim 1, wherein determining the first anatomical orientation comprises determining an orientation of a coronal plane of the subject based on the at least three locations.

6. The apparatus of claim 5, wherein the operations further comprise receiving information indicating a pelvic tilt angle;
   wherein determining the orientation of the coronal plane of the subject comprises determining the orientation of the coronal plane using information indicating the pelvic tilt angle.

7. The apparatus of claim 5, wherein receiving data indicating locations on the pelvis comprises receiving data indicating at least two locations on the pelvis that are located substantially along a medial-lateral axis; and
   wherein determining the second anatomical orientation comprises determining an orientation of a transverse plane of the subject based on the data indicating at least two locations on the pelvis, the orientation of the transverse plane being orthogonal to the orientation of the coronal plane of the subject.

8. The apparatus of claim 7, wherein the at least two locations include locations corresponding to a left anterior superior spine of an ilium of the pelvis and a right anterior superior spine of the ilium.

9. The apparatus of claim 1, wherein the data indicating the position of the reference device configured to move with the pelvis of the subject indicates a position of the reference device corresponding to a first position of the subject lying on the reference surface.

10. The apparatus of claim 9, wherein the data indicating the position of the reference device configured to move with the pelvis of the subject indicates a position of the reference device corresponding to a second position of the subject that is different from the first position; and
   wherein the operations further comprise:
      adjusting the anatomical orientations based on the position of the reference device corresponding to the second position;
      determining a position of a surgical axis relative to the adjusted anatomical orientations; and
      determining a position of a tool relative to the surgical axis based on the position of the reference device corresponding to the second position of the subject.

11. The apparatus of claim 1, wherein receiving the data indicating the position of the reference device comprises receiving data indicating a position of an electromagnetic field sensor or a fiducial of the reference device.

12. The apparatus of claim 1, wherein the expected posture is a posture of the subject lying in a supine position on the substantially planar reference surface;
   wherein receiving the data indicating locations on the pelvis comprises receiving data indicating locations corresponding to a left anterior superior spine of an ilium of the pelvis and a right anterior superior spine of the ilium;
   wherein determining the first anatomical orientation comprises:
      receiving data indicating a pelvic tilt angle; and
      determining an orientation of a coronal plane of the subject based on the at least three different points on the substantially planar reference surface and the data indicating the pelvic tilt angle; and
   wherein determining the second anatomical orientation comprises determining an orientation of a medial-lateral axis or transverse plane of the subject based on the locations corresponding to the left anterior superior spine of the ilium and the right anterior superior spine of the ilium.

13. The apparatus of claim 12, wherein the operations further comprise:
   determining a surgical trajectory for the subject using the first anatomical orientation and the second anatomical orientation;
   receiving data indicating the position of a surgical tool relative to the position of the reference device while the subject is in a lateral position;
   determining an orientation of the surgical tool relative to the surgical trajectory based on the data indicating the position of the surgical tool relative to the position of the reference device while the subject is in the lateral position; and
   outputting data indicating the orientation of the surgical tool relative to the surgical trajectory.

14. The apparatus of claim 1, wherein receiving data indicating the at least three locations on the substantially planar reference surface comprises receiving data indicating at least three locations on a surgical table on which the subject is resting; and
   wherein determining the first anatomical orientation comprises determining an orientation of a coronal plane of the subject at a particular relationship from a plane indicated by the at least three locations on the surgical table.

15. The apparatus of claim 1, wherein the operations further comprise:
   determining a predetermined position for the surgical tool relative to the subject; and
   determining an angle of the surgical tool relative to the preferred position for the surgical tool based on the registered first anatomical orientation and the registered second anatomical orientation; and
   providing, for output on the display, an indication of the angle of the surgical tool relative to the predetermined position for the surgical tool.

16. The apparatus of claim 6, wherein receiving information indicating a pelvic tilt angle comprises receiving information indicating an angle between (i) a line defined between a hip and shoulder of the subject, and (ii) a reference surface.

17. An apparatus comprising:
   one or more processing devices; and
   one or more data storage devices storing instructions that are operable, when executed by the one or more processing devices, to cause the one or more processing devices to perform operations comprising:
      receiving data indicating a position of a reference device configured to move with a pelvis of a subject, wherein the indicated position is a position of the reference device while the subject is in a supine position on a surgical table;
      receiving data indicating at least three locations on the surgical table that are determined while the subject is in the supine position on the surgical table;
      receiving data indicating locations on the pelvis;
      determining a coronal plane of the subject based on the data indicating the at least three locations on the reference surface;
      determining an orientation of a transverse plane of the subject based on the data indicating the locations on the pelvis;
      registering the coronal plane and the transverse plane to the reference device;
      determining a position of a surgical tool relative to the subject using the registered coronal plane and transverse plane; and
      providing, for output on a display in communication with the apparatus, an indication of the determined position of the surgical tool relative to the subject.

18. The apparatus of claim 17, wherein the operations further comprise:
   determining a surgical trajectory based on the first anatomical orientation and the second anatomical orientation;

determining a position of a tool relative to the surgical trajectory based on a position of the reference device; and outputting data indicating the position of the tool relative to the surgical trajectory.

19. The apparatus of claim 18, wherein determining the surgical trajectory based on the first anatomical orientation and the second anatomical orientation comprises determining an orientation at a predetermined inclination angle and a predetermined anteversion angle relative to the first anatomical orientation and the second anatomical orientation.

20. The apparatus of claim 17, wherein the operations further comprise receiving information indicating a pelvic tilt angle; and wherein determining the orientation of the coronal plane of the subject comprises determining the orientation of the coronal plane using information indicating the pelvic tilt angle.

* * * * *